(12) United States Patent
Cubicciotti

(10) Patent No.: US 7,128,875 B2
(45) Date of Patent: Oct. 31, 2006

(54) SIGNAL PROCESSING DEVICES COMPRISING BIOLOGICAL AND BIO-MIMETIC COMPONENTS

(76) Inventor: Roger S. Cubicciotti, 258 Midland Ave., Montclair, NJ (US) 07042

(*) Notice: Subject to any disclaimer, the term of this patent is extended or adjusted under 35 U.S.C. 154(b) by 0 days.

(21) Appl. No.: 10/020,151

(22) Filed: Dec. 18, 2001

(65) Prior Publication Data

US 2003/0134325 A1 Jul. 17, 2003

Related U.S. Application Data

(60) Division of application No. 08/928,507, filed on Sep. 12, 1997, now Pat. No. 6,342,389, which is a continuation-in-part of application No. 08/600,359, filed on Feb. 13, 1996, now abandoned, which is a continuation-in-part of application No. 08/420,726, filed on Apr. 10, 1995, now Pat. No. 5,695,990.

(51) Int. Cl.
*B32B 5/02* (2006.01)
(52) U.S. Cl. ............... 422/82.05; 422/82.07; 422/82.08; 422/82.11; 436/172; 250/458.1; 250/459.1
(58) Field of Classification Search ........... 422/82.05, 422/82.07, 82.08, 82.11; 436/172; 250/458.1, 250/459.1
See application file for complete search history.

(56) References Cited

U.S. PATENT DOCUMENTS

| | | | |
|---|---|---|---|
| 3,934,369 A | 1/1976 | Rebeiz | |
| 4,320,050 A | 3/1982 | Rebeller et al. | |
| 4,520,110 A | 5/1985 | Stryer et al. | |
| 4,542,104 A | 9/1985 | Stryer et al. | |
| 4,666,862 A | 5/1987 | Chan | |
| 4,707,454 A * | 11/1987 | Hendrix | 436/546 |
| 4,745,285 A | 5/1988 | Recktenwald et al. | |
| 4,857,474 A * | 8/1989 | Waterbury et al. | 436/501 |
| 4,859,582 A | 8/1989 | Stryer et al. | |
| 5,037,615 A * | 8/1991 | Kane | 422/82.08 |
| 5,055,556 A | 10/1991 | Stryer et al. | |
| 5,171,846 A | 12/1992 | Gupta | |
| 5,272,257 A | 12/1993 | Gupta | |
| 5,643,585 A * | 7/1997 | Arad et al. | 424/401 |
| 5,695,990 A * | 12/1997 | Cubicciotti | 435/317.1 |
| 6,020,212 A * | 2/2000 | Mathis | 436/546 |

OTHER PUBLICATIONS

Apt et al., "Characterization and Transcript Analysis of the Major Phycobiliprotein Subunit Genes from *Aglaothamnion neglectum* (Rhodophyta)", *Plant Molecular Biology* 21:27-38 (1993).
Apt et al., "Genes Encoding Phycobilisome Linker Polypeptides on the Plastid Genome of *Aglaothamnion neglectum* (Rhodophyta)", *Phtosynthesis Research* 35:235-245 (1993).

(Continued)

*Primary Examiner*—Jill Warden
*Assistant Examiner*—Neil Turk
(74) *Attorney, Agent, or Firm*—Hunton & Williams LLP

(57) ABSTRACT

This invention provides modified phycobilisomes and phycobilisome complexes that are supramolecular complexes with diverse spectral properties, and which may optionally be immobilized on a manufactured solid support. The invention provides a versatile set of highly sensitive signal-generating systems and conjugates that may be used as highly detectable tracers and labels, or in biotransducers comprising phycobilisomes or phycobilisome complexes, and also provides methods for performing specific binding assays using signal-generating systems comprising phycobilisomes as detectable labels. The embodiments of the invention provide the art with an extremely sensitive, nonisotopic detection means for assaying analytes and for sensing molecular events and environmental conditions.

27 Claims, 6 Drawing Sheets

OTHER PUBLICATIONS

Cohen-Bazire et al., "Chapter 7: Phycobilisomes: Composition and Structure", *The Biology of Cyanobacteria*, Carr NG and Whitton BA (eds), Univ. of Cal Press, Berkeley & LA, pp. 143-190 (1982).

Bennett et al., "Properties of Subunits and Aggregates of Blue-Green Algal Biliproteins", *Biochemistry 10* (19):3625-3634 (1971).

Brimble et al., "Pigment Orientation and Excitation Energy Transfer in *Porphyridium cruentum* and *Synechococcusi* sp. PCC 6301 Cross-Linked in Light State 1 and Light State 2 with Glutaraldehyde", *Biochem. & Biophys. Acta*, 973:315-323 (1989).

Bruce et al., "State Transitions in a Phycobilisome-Less Mutant of th eCyanobacterium *Synechococcus* sp. PCC 7002", *Biochimica et Biophysica Acta* 974:66-73 (1989).

Bruns et al., "Molecular Characterization of Phycobilisome Regulatory Mutants of *Fremyella diplosiphon*", *J. Bacteriology* 171(2):901-908 (1989).

Bryant et al., "Characterization of the Biliprotiens of *Gloeobacter violaceus*", *Arch. Microbilogy* 129:190-198 (1981).

Bryant, "Phycobilisomes of *Synechococcus* Sp. PCC 7002, *Pseudanabaena* SP. PCC 7409, and *Cyanophora paradaxa*: an Analysis by Molecular Genetics", *Photosynthetic Light-Harvesting Systems*, Scheer H, Schneider S. (eds), Walter de Gruyter & Co., NYC (1988).

Canaani et al., "Formation of Hybrid Phycobilisomes by Association of phycibiliproteins from *Nostoc* and *Fremyella*", *Proc. Natl. Acad. Sci. USA* 79:5277-5281 (1982).

Canaani et al., "Reassembly of Phycobilisomes from Allophycocyanin and a Phycocyanin-Phycoerythrin Complex", *FEBS Letters* 115(2):225-229 (1980).

Collier et al., "A Small Polypeptide Triggers Complete Degradation of Light-Harvesting Phycobiliprotiens in Nutrient-Deprived Cyanobacteria", *The EMBO Journal* 13(5):1039-1047 (1994).

Conley et al., "Genes Encoding Major Light-Harvesting Polypeptides are Clustered on the Genome of the Cyanobacterium *Fremyella diplosiphon*", *Proc. Natl. Acad. Sci, USA* 83:3924-3928 (1986).

Gagliano et al., "Orientation of Pigments in Phycobilisomes of *Porphyridium* sp. Lewin. A Linear Dichroism Study Utilizing Electric and Gel Orientation Methods", *Biochem. & Biophys. Acta* 808:455-463 (1985).

Gantt, "Phycobilisomes: Assessment of the Core Structure and Thylakoid Interaction", *Light-Energy Transduction in Photosynthesis: Higher Plant and Bacterial Models*, Stevens SE, Bryant DA (eds), American Society of Plant Physiologists, pp. 91-101 (1988).

Gantt et al., "Photosystem II-Phycobilisome Complex Preparations", *Methods in Enzymology* 267:286-290 (1988).

Gantt et al., "Phycobiliprotein Localization in Algae", *Energy Conversion by the Photosynthetic Apparatus*, No. 19:393-405 (1967).

Gantt, "Properties and Ultrastructure of Phycoerythrin from *Porphyridium cruentum*", *Plan Physiol.* 44:1629-1638 (1969).

Gantt, "Phycobilisomes from Blue-Green and Red Algae", *Plant Physiol.* 63:615-620 (1979).

Gantt et al., "Phycobilisomes of *Porphyridium cruentum*", *J. Cell Biol.* 54:313-324 (1972).

Gantt et al., "Granules Associated with the Chloroplast Lamellae of *Porphyridium Cruentum,*" *J. Cell Biol.* 29:423-434 (1966).

Gantt et al., "The Ultrastructure of *Porphyridium cruentum*", *J. Cell Biol.* 26:365-381 (1965).

Gingrich et al., "Core Substructure in Cyanobacterial Phycobilisomes", *J. Cellular Biochemistry* 22:1-14 (1983).

Glazer et al., "Kinetics of Energy Flow in the Phycobilisome Core", *Science* 230:1051-1053 (1985).

Glazer, "Light Harvesting by Phycobilisomes", *Ann. Rev. Biophys. Chem.* 14:47-77 (1985).

Glazer, "Light Guides", *J. Biological Chemistry* 264(1):1-4 (1989).

Glazer, "Phycobilisome: A Macromolecular Complex Optimized for Light Energy Transfer", *Biochimica et Biophysica Acta* 768:29-51 (1984).

Glazer, "Structure and Molecular Organization of the Photosynthetic Accessory Pigments of Cyanobacteria and Red Algae", *Mol. Cell Biochem.* 18:125-139 (1977).

Glazer et al., "Fluorescent Tandem Phycobiliprotein Conjugates", *Biophys. J. Biophysical Society* 43:383-386 (1983).

Glazer et al., "Formation of Hybrid Proteins from the $\alpha$ and $\beta$ Subunits of Phycocyanins of Unicellular and Filamentous Blue-Green Algae", *J. Biol. Chem.* 248:663-671 (1973).

Glick et al., "Role of Colorless Polypeptides in Phycobilisome Reconstitution from Separated Phycobiliproteins", *Plants Physiol.* 69:991-997 (1982).

Grossman et al., "A Rapid Procedure for the Isolation of Intact Phycobilisomes", *Carnegie Inst. Wash. Yearbook* 82:116120 (1983).

Guglielmi et al., "The Structure of *Gloeobacter violaceus* and its Phycobilisomes", *Arch. Microbiology* 129:181-189 (1981).

Houmard et al., "Genes Encoding Cor Components of the Phycobilisome in the Cyanobacterium *Calothrix* sp. Strain PCC 7601: Occurrence of a Multigene Family", *J. Bacteriology* 170(12):5512-5521 (1988).

Katoh et al., "Photosynthetic Vesicles with Bound Phycobilisomes from *Anabaena variabilis*", *Biochimica et Biophysica Acta* 546:383-393 (1979).

Katoh, "Phycobilisome Stability", *Methods in Enzymology* 167:313-318 (1988).

Kirilovsky et al., "Functional Assembly *in Vitro* of Phycobilisomes with Isolated Photosystem II Particles of Eukaryotic Chloroplasts", *J. Biol. Chem.* 261(26):12317-12323 (1986).

Kronick et al., "Immunoassay Techniques with Fluorescent Phycobiliprotein Conjugates", *Clin. Chem.* 29/9:1582-1586 (1983).

Lipschultz et al., "Association of Phycoerythrin and Phycocyanin: *In Vitro* Formation of a Functional Energy Transferring Phycobilisome Complex of *Porphyridium sordidum*", *Biochemistry* 20:3371-3376 (1981).

Clement-Metral et al., "Fluorescence Transfer in Glutaraldehyde Fixed Particles of the Red Alga *Porphyridium cruentum* (N)", *FEBS Letters* 12(4):225-228 (1971).

Clement-Metral et al., "Isolation of Oxygen-Evolving Phycobilisome-Photosystem II Particles from *Porphyridium cruentum*", *FEBS Letters* 156(1):185-188 (1983).

Rosinski et al., "Phycobilisome Ultrastructure and Chromatic Adaptation in *Fremyella diplosiphon,*" *Ann. Bot.* 47:1-12 (1981).

Shen et al., "*Synechocystis* sp PCC 6803 Strains Lacking Photosystem I and Phycobilisome Function", *The Plant Cells* 5:1853-1863 (1993).

Sofrova et al., "Crosslinking of Isolated Phycobilisomes with Dimethyl Suberimidate", *Photosynthesis III. Structure and Molecular Organisation of the Photosynthetic Aparatus*, edited by George Akoyunoglou, Balaban International Science Services, Philadelphia, PA (1981).

Yamanaka et al., "Molecular Architecture of a Light-Harvesting Antenna", *J. Biological Chemistry* 257(8):4077-4086 (1982).

Wolfe et al., "Evidence for a Common Origin of Chloroplasts with Light-Harvesting Complexes of Different Pigmentation", *Nature* 367:566-568 (1994).

Redecker et al., "Core Substructure of the Hemiellipsoidal Phycobilisome From the Red Alga Porphyridium Cruentum", *European J. Cell Biology* 62:442-450 (1993).

Skibinski et al., "Spectral Properties of *Mastigocladus laminosus* Phycobilisomes Embedded in Poly(vinyl alcohol) Filmes", *J. Photochem. Photobiol. B: Biol.* 23:213-223 (1994).

Frackowiak et al., "Analysis of Time-Resolved Emission Spectra of Oriented Phycobilisomesw" *Biophysiucal Chemistry* 42:153-161 (1992).

Lu Rong-Zhao et al., "Studies in the Fluorescence Emission Spectra and Energy Transfer of Phycobilisomes from Spirulina Platensis in the Course of Dissociation" *Research in Photosynthesis* I:61-64 (1992).

Gantt et al., "Phycobilisomes: A Terminal Acceptor Pigments in Cyanobacteria and Red Algae", *Molecular Biology of the Photosynthetic Apparatus*, 1985 Cold Spring Harbor laboratory pp. 223-229.

Gantt, "Phycobilisomes", *Photosynthesis III: Photosynthetic Membranes and Light Harvesting Systems* (L.A. Strachelin and C.J. Arntzen, eds.), pp. 260-268, Spring-Verlag, NY.

Grossman et al., "The Phycobilisome, a Light-Harvesting Complex Responsive to Environmental Conditions", *Microbiological Reviews* 57(3):725-749 (1993).

Rigbi et al., "Cyanobacterial Phycobilisomes: Selective Dissociation Monitored by Fluorescence and Circular Dichroism", *Proc. Natl. Acad. Sci. USA* 77(4):1961-1965 (1980).

Biggins, "Mechanism of the Light State Transition in Photosynthesis", *Biochimica et Biophysica Acta* 724:111-117 (1983).

Glazer et al., "Phycofluor Probes", *TIBS*, Oct. 1994, pp. 423-427.

Glazer, "Phycobilisomes: Structure and Dynamics of Energy Flow", *Molecular Biology of the Photosynthetic Apparatus*, 1985 Cold Spring Harbor Laboratory, pp. 231-239.

\* cited by examiner

SIGNAL PROCESSING DEVICES COMPRISING BIOLOGICAL AND BIO-MIMETIC COMPONENTS

This application is a divisional application of U.S. application Ser. No. 08/928,507, filed Sep. 12, 1997 now U.S. Pat. No. 6,342,389; which is a continuation in part application of U.S. application Ser. No. 08/600,359, filed Feb. 13, 1996 now abandoned; which is a continuation in part application of U.S. application Ser. No. 08/420,726, filed Apr. 10, 1995 (now U.S. Pat. No. 5,695,990).

BACKGROUND OF THE INVENTION

Phycobilisomes are complexes of phycobiliproteins and colorless polypeptides which function as the major light harvesting antennae in blue-green and red algae (Gantt, (1975) "Phycobilisomes: light harvesting pigment complexes," *BioScience* 25:781–788). Naturally-occurring phycobilisomes from different organisms share a number of common properties, including: (1) extremely high "complex molecular weights" (5–20×10$^6$ daltons) i.e., the weight of one mole of a phycobilisome complex comprised of multiple molecules; (2) multiple absorption maxima in the visible range of the electromagnetic spectrum; (3) high molar absorptivities ($e_{max}$>10$^7$ M$^{-1}$·cm$^{-1}$); (4) efficient (>90%) directional vibrational energy transfer among constituent phycobiliproteins, commonly from one or more sensitizing species to a terminal acceptor capable of fluorescence; (5) large Stokes shifts relative to isolated phycobiliproteins; (6) high quantum yields of constituent phycobiliproteins; (7) high solubility in aqueous buffers; (8) allophycocyanin-containing core structures; and (9) precisely defined phycobiliprotein and linker polypeptide composition and supramolecular organization.

Morphologically, phycobilisomes are complex assemblies of oligomeric phycobiliprotein discs arranged in ordered stacks referred to as "rods". In general, several arm-like rods radiate out from a core assembly, also comprised of rods. Phycobilisomes from different organisms are morphologically and stoichiometrically diverse, having different numbers and types of constituent phycobiliproteins and rods. In general, peripheral rods are comprised of phycoerythrocyanin, phycoerythrin, and/or phycocyanin and associated linker proteins, and the core is comprised of allophycocyanin and associated linker proteins. The colorless polypeptides are involved in the assembly and positioning of the phycobiliproteins within the phycobilisomes for proper stability and energy transfer. The major criterion for the functional integrity of these complexes is the demonstration that they exhibit highly efficient transfer of energy between component phycobiliproteins, for example, in *Porphyridium cruentum* phycobilisomes from phycoerythrin (PE) to phycocyanin (PC) and finally to allophycocyanin (APC).

Supramolecular complexes comprising phycobilisomes are well-known in the art, as evidenced by the substantial body of literature on preparative methods (e.g., Gantt, E. 1986, "Phycobilisomes. In: Photosynthesis III: Photosynthetic Membranes and Light Harvesting Systems" (L. A. Staehelin and C. J, Arntzen, eds.), pp. 260–268, Springer-Verlag, N.Y.; Grossman, A. R. et al. 1993, "The phycobilisome, a light-harvesting complex responsive to environmental conditions," *Microbiological Reviews* 57:725–749; Hiller, et al., 1982, "Isolation of intact detergent-free phycobilisomes by trypsin." *FEBS Lett.* 156:180–184), rod and core subassemblies (e.g., Lundell, et al. 1983a, "Molecular architecture of a light-harvesting antenna: core substructure in *Synechococcus* 6301 phycobilisomes: two new allophycocyanin and allophycocyanin B complexes," *J. Biol. Chem.*, 258:902–908; Lundell, et al., 1983b, "Molecular architecture of a light-harvesting antenna: quaternary interactions in the *Synechococcus* 6301 phycobilisome core as revealed by partial tryptic digestion and circular dichroism studies," *J. Biol. Chem.*, 258:8708–8713; Lundell, et al., 1983c, "Molecular architecture of a light-harvesting antenna: structure of the 18S core-rod subassembly of the *Synechococcus* 6301 phycobilisome," *J. Biol. Chem.*, 258: 894–901; Glazer, A. N. 1985a, "Light harvesting by phycobilisomes," *Annual Rev. Biophys. and Biophys. Chem.*, 14:47–77), phycobilisome-photosystem complexes (e.g., Diner, B. A. 1979, "Energy transfer from phycobilisomes to photosystem II reaction centers in wild type *Cyanidium caldarium,*" *Plant Physiol.*, 63:30–34; Gantt E, et al. (1988), "Photosystem II-phycobilisome complex preparations," *Meth. Enzymol.* 167, 286–290; Clement-Metral, J. D. and Gantt (1983a), "Isolation of oxygen-evolving phycobilisome-photosystem II particles from *Porphyridium cruentum,*" *FEBS Letters* 156:185–188; Clement-Metral J D, et al. (1983b), "A photosystem II-phycobilisome preparation from the red alga *Porphyridium cruentum*: oxygen evolution, ultrastructure, and polypeptide resolution," *Arch. Biochem. Biophys.* 238:10–17; Kirilovsky D, et al. (1986). "Functional assembly in vitro of phycobilisomes with isolated photosystem II particles of eukaryotic chloroplasts," *J. Biol. Chem.*, 261:12317–12323), phycobilisome-membrane preparations (e.g., Clement-Metral, J. D., et al. (1971), "Fluorescence transfer in glutaraldehyde fixed particles of the red alga *Porphyridium cruentrum* (N)," *FEBS Letters* 12:225–228), phycobilisome dissociation (e.g., Rigbi, et al. (1980), "Cyanobacterial phycobilisomes: Selective dissociation monitored by fluorescence and circular dichroism." *Proc. Natl. Acad. Sci. USA,* 77:1961–1965) and reconstitution (e.g., Gantt, et al. (1979), "Phycobilisomes from blue-green and red algae: Isolation criteria and dissociation characteristics," *Plant Physiology* 63:615–620; Kirilovsky et al. (1986), Glick, et al. (1983), "Role of the colorless polypeptides in phycobilisome reconstitution from separated pycobiliproteins," *Plant Physiol.*, 69:991–997), genetic modifications (e.g., Bryant, D. A., 1991, "Cyanobacterial phycobilisomes: progress toward complete structural and functional analysis via molecular genetics," In L. Bogorad and I. K. Vasil (ed.), *Cell Culture and Somatic Genetics of Plants. Molecular Biology of Plastids and Mitochondria*, Vol. 7, pp. 257–300, Academic Press, San Diego, Calif.); Yamanaka, et al. (1978), "Cyanobacterial phycobilisomes. Characterization of the phycobilisomes of *Synechococcus* sp. 6302," *J. Biol. Chem.*, 253:8303–8310; Yamanaka, et al. (1980), "Molecular architecture of a light-harvesting antenna. Comparison of wild type and mutant *Synechococcus* 6301 phycobilisomes," *J. Biol. Chem.*, 255:11004–11010), and environmental effects (e.g., Grossman et al. (1993)), including chromatic adaptation (e.g., Bryant, et al. 1981, "Effects of chromatic illumination on cyanobacterial phycobilisomes: Evidence for the specific induction of a second pair of phycocyanin subunits in *Pseudanabaena* 7409 grown in red light," *Eur. J. Biochem.* 119:415–424).

Isolated phycobilisomes readily dissociate into free phycobiliproteins and a variety of phycobiliprotein complexes under all but the most favorable conditions. Low to moderate ionic strength (<0.5 M phosphate), low phycobilisome concentration (<1 mg/ml), and low and high temperatures lead to dissociation of phycobilisomes (Katoh, (1988) *Methods in Enzymology,* 162:313–318; Gantt et al., (1979)).

Freezing of algae is also reported to lead to destruction of phycobilisomes (Gantt et al., (1972) *Journal of Cell Biology*, 54:313–324).

Isolated phycobiliproteins, the component fluorescent proteins of phycobilisomes, have been used as labels in immunoassays. See e.g., Stryer et al., U.S. Pat. No. 4,520,110 and Kronick et al. (1983) *Clinical Chemistry*, 29:1582–1586. However, because of the difficulty in isolating and manipulating intact phycobilisomes, the art has not recognized that these macromolecular assemblies could be similarly utilized. Because the signal which phycobilisomes can provide is theoretically so much larger than that of isolated phycobiliproteins, there is a need in the art for methods of treating phycobilisomes so that they can be used as detectable markers for a host of assays and other applications.

SUMMARY OF THE INVENTION

One object of this invention is to provide supramolecular complexes with diverse spectral properties for use as highly detectable tracers and labels.

Another object of this invention is to provide a versatile set of highly sensitive signal-generating systems and conjugates for use in, inter alia, various assay methods.

Yet another object of this invention is to provide biotransducers comprising phycobilisomes or phycobilisome complexes immobilized on a manufactured solid support.

Still another object of this invention is to provide methods for performing specific binding assays using signal-generating systems comprising phycobilisomes as detectable labels. These and other intentions of this invention are achieved by one or more of the following embodiments.

In one embodiment, this invention provides an isolated, soluble, stabilized phycobilisome comprising two or more phycobiliproteins specifically connected by at least one linker polypeptide. The stabilized phycobilisome of this embodiment may comprise at least one peripheral rod, or a core complex and no peripheral rods, or a core complex, and at least one disc. In one mode, the stabilized phycobilisome of this embodiment comprises an anchor polypeptide. In a particular mode, the different proteins making up the stabilized phycobilisome of this embodiment are not all found in a single algal strain, but rather are proteins whose sequences are encoded by more than one distinct algal strain; in other words, some of the proteins making up the phycobilisomes of this mode may originally derive from an algal strain different from the strain that is the source of other proteins in the phycobilisome. In another particular mode, the stabilized phycobilisome is reconstituted from a mixture containing phycobilisome components, which may include isolated phycobiliproteins and/or isolated linker polypeptides, and optionally partially reconstituted phycobilisomes. In a preferred mode of this embodiment, the stabilized phycobilisome is modified by covalent attachment of desired chemical moieties, the chemical moieties optionally being attached to a particular portion of the phycobilisome. In yet another mode, the isolated, stabilized phycobilisome of this embodiment is functionally coupled to another signal-generating system.

In another embodiment, this invention provides a phycobilisome conjugate comprising a phycobilisome conjugated to a molecular species selected from the group consisting of ligands, receptors, and signal-generating molecules, where the phycobilisome comprises a plurality of phycobiliproteins specifically connected by at least one linker polypeptide, the molecular species preferably being attached to a single type of phycobiliprotein or a single type of linker polypeptide or an anchor peptide. Alternatively, the molecular species may be attached to a particular portion of the phycobilisome. In one mode of this embodiment, the phycobilisome comprises at least one protein encoded by each of at least two different algal strains. In an alternative mode of this embodiment, the phycobilisome is reconstituted from a mixture containing isolated phycobiliproteins, isolated linker proteins, or a mixture thereof. In yet another mode of this embodiment, the phycobilisome is functionally coupled to a signal-generating system. The molecular species conjugated to the phycobilisome may be, for example, streptavidin, avidin, an antibody, biotin, a drug, an antigen, a hapten, a nucleic acid, a carbohydrate, or a lectin.

In yet another embodiment, this invention provides an isolated, functionally intact phycobilisome comprising a plurality of phycobiliproteins specifically connected by at least one linker polypeptide, where the phycobilisome is immobilized on a solid support. In a preferred mode of this embodiment, the immobilized phycobilisome is stabilized. In another preferred mode, the immobilized phycobilisome is covalently attached to a molecular species selected from the group consisting of ligands, receptors, and signal-generating molecules, and more preferably, the molecular species is attached to one type of constituent phycobilisome protein or to a particular portion of the phycobilisome. In one mode of this embodiment, the immobilized phycobilisome comprises at least one protein encoded by each of at least two different algal strains. In an alternative mode of this embodiment, the immobilized phycobilisome is reconstituted from a mixture containing isolated phycobiliproteins, isolated linker proteins, or a mixture thereof. In yet another mode of this embodiment, the immobilized phycobilisome is functionally coupled to another signal-generating system. Alternatively, the immobilized phycobilisome may be a functional component of a biotransducer. The solid support may be selected from the group consisting of a synthetic membrane, a polymer, a microparticle, silicon, and glass. In a particular mode of this embodiment, the invention provides a manufactured solid support containing a plurality of immobilized phycobilisomes, where the phycobilisomes are immobilized on the solid support in a structurally ordered arrangement thereby forming a pattern on the solid support. In an alternative mode of this embodiment, the invention provides a manufactured solid support containing a plurality of immobilized phycobilisomes, where the phycobilisomes are all immobilized on the solid support in the same orientation with respect to the solid support.

In still another embodiment, this invention provides an input system for a transducer comprising conversion means for receiving ultraviolet or visible light and directionally transferring light energy of this light; and coupling means for receiving the directionally transferred light energy and delivering the light energy to a transducer. Preferably, the coupling means comprises an optical fiber or a waveguide; preferably, the conversion means comprises a phycobilisome.

In yet another embodiment, this invention provides an environmentally responsive optical sensor comprising conversion means for receiving ultraviolet or visible light and directionally transferring light energy of this light, such that transfer of light energy is dependent on an environmental condition; and sensor means for receiving the directionally transferred light energy and producing an indication of the environmental condition. In particular, one or more environmental conditions may affect a characteristic of the transferred light energy, such as the energy level of transferred light energy. In a preferred mode of this embodiment, the directionally transferred light energy comprises a photon of a particular energy level, the energy level being dependent upon the environmental condition. More preferably, the conversion means comprises a phycobilisome.

In still another embodiment, this invention provides a system for processing a light signal comprising conversion means for receiving ultraviolet or visible light and directionally transferring light energy of this light; and processing means for receiving and processing the directionally transferred light energy. In a preferred mode of this embodiment, the processing means comprises an optical fiber operative to transmit the light signal and/or a photosensor. Preferably, the directionally transferred light energy comprises a photon, and/or the conversion means comprises a phycobilisome.

In yet another embodiment, this invention provides a method for performing a specific binding assay comprising contacting a sample comprising an analyte with a specific binding partner; determining the amount of the analyte present in the sample by means of its ability to specifically bind to the specific binding partner, where a component of the assay is detectably labeled with a signal-generating system comprising phycobilisomes, the phycobilisomes being self-assembling complexes of phycobiliproteins and linker proteins, where each phycobilisome comprises at least one rod. The detectably-labeled assay component is selected from the group consisting of a specific binding partner of the analyte, reagent molecules having the same chemical identity as the analyte, and reagent molecules which compete with the analyte for specific binding to the specific binding partner. Typically, the competitive reagent molecules will have the same binding specificity as the analyte, and optionally they may have similar affinity for the specific binding partner. In a preferred mode of this embodiment, the analyte or its specific binding partner is attached to a solid phase. The solid phase may be, for example, a synthetic membrane, a polymer, a microparticle, silicon, or glass, and the analyte may be, for example, a nucleic acid, a drug, a ligand, an antigen, a hapten, an antibody, or a carbohydrate.

These and other embodiments of the invention provide the art with an extremely sensitive, nonisotopic detection means for assaying analytes and for sensing molecular events and environmental conditions. Unlike enzymatic labels, phycobilisomes can be quantitatively detected without accessory substrates, chromogens, cofactors, or timed incubations. Alternatively, phycobilisomes can be functionally coupled to enzymes or other signal-generating molecules to amplify or transduce molecular events, thereby generating a more preferred assay signal or transducer output.

BRIEF DESCRIPTION OF THE DRAWINGS

Features of various embodiments of the invention are described in the drawings, which should be interpreted in light of this application as a whole.

DETAILED DESCRIPTION OF THE PREFERRED EMBODIMENTS

Figure 1:
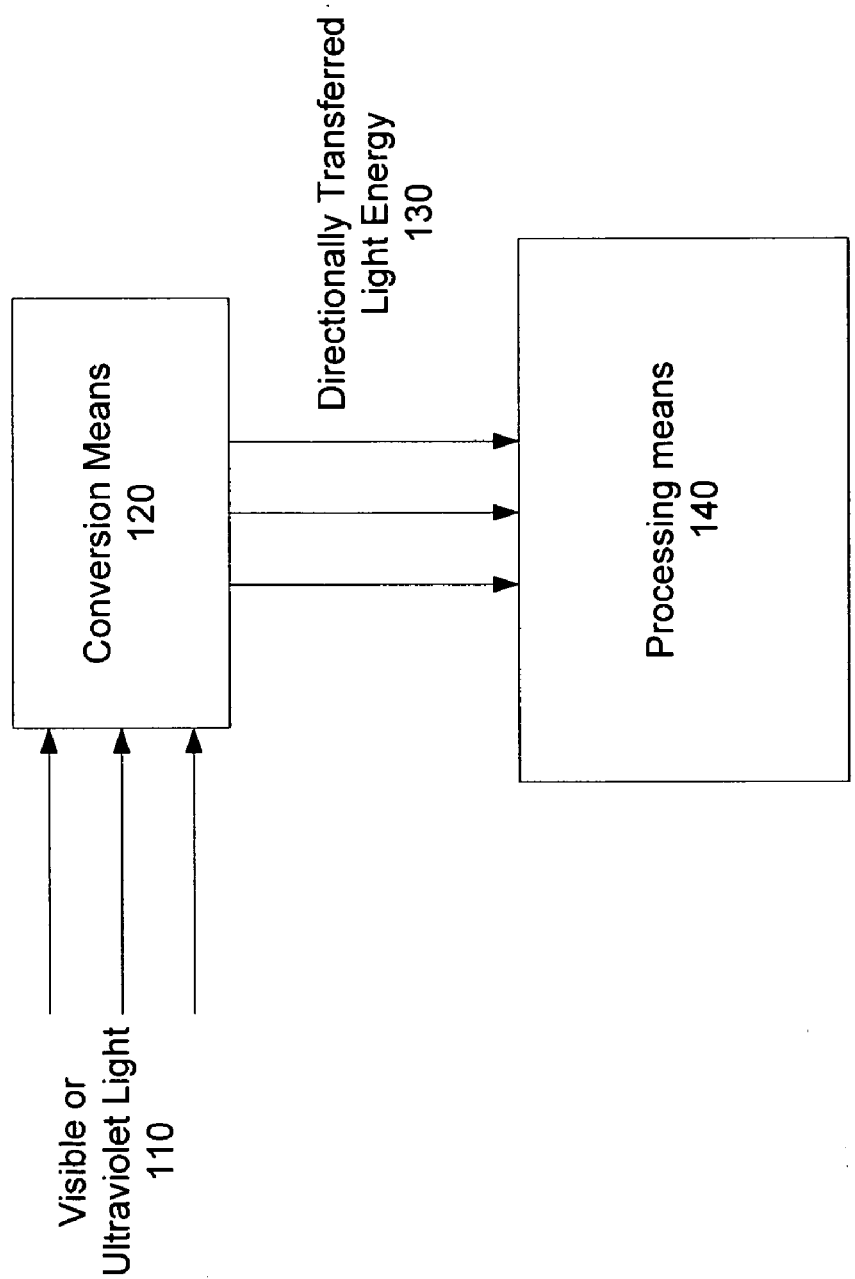
FIG. 1 shows conversion means 120 receiving visible or ultraviolet light 110. The conversion means 120 may comprise a phycobilisome. The conversion means 120 passes directionally transferred light energy 130 to processing means 140. Processing means 140 may comprise an optical fiber, photosensor, waveguide, and/or optoelectronic device.
Figure 2:
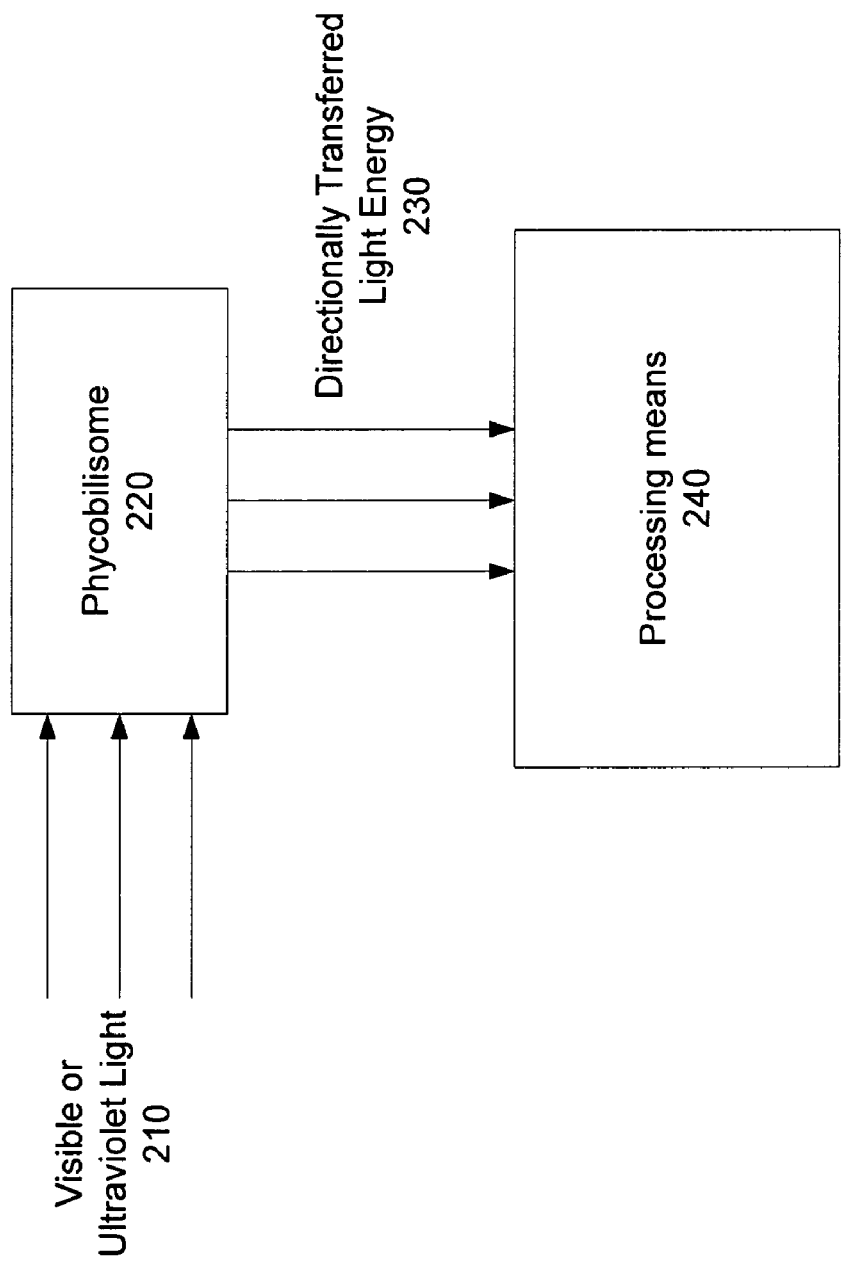
FIG. 2 shows a phycobilisome 220 receiving visible or ultraviolet light 210. The phycobilisome may pass directionally transferred light energy 230 to processing means 240. Processing means 240 may comprise an optical fiber, photosensor, phycobilisome, waveguide, and/or optoelectronic device.
Figure 3:
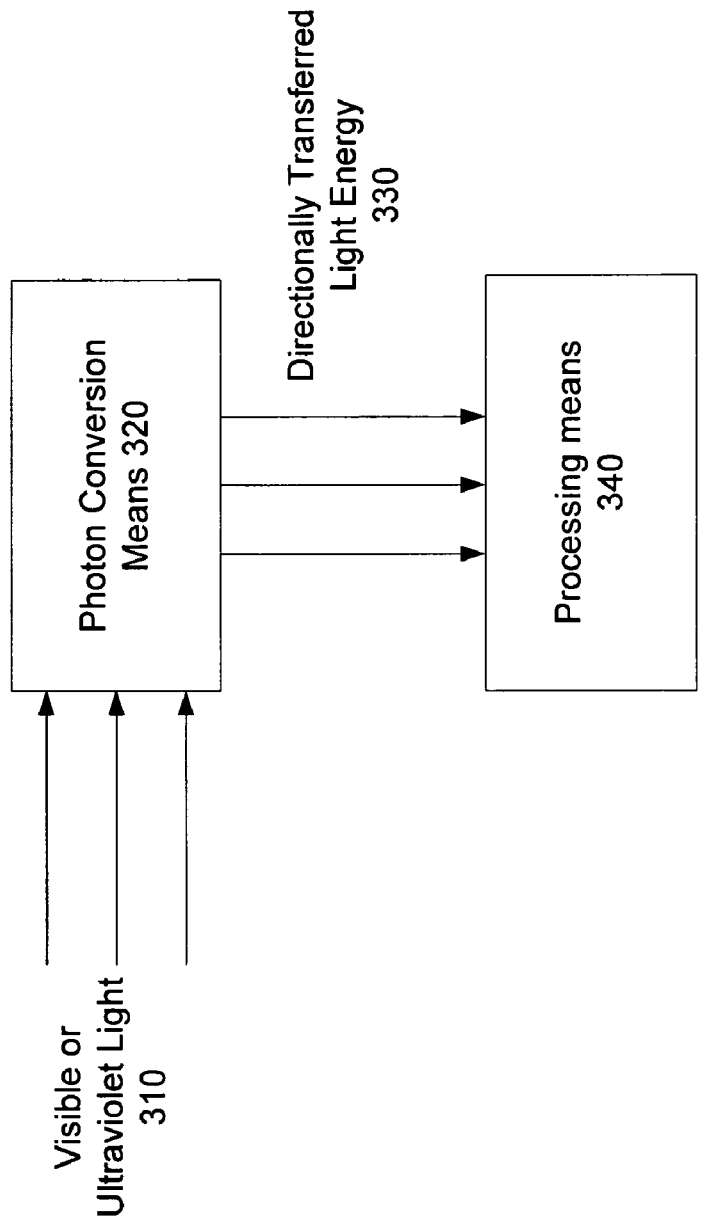
FIG. 3 shows a photon conversion means 320 receiving visible or ultraviolet light 310. The photon conversion means 320 may comprise a supramolecular light-absorbing structure, such as a phycobilisome. The photon conversion means 320 passes directionally transferred light energy 330 to processing means 340.
Figure 4:
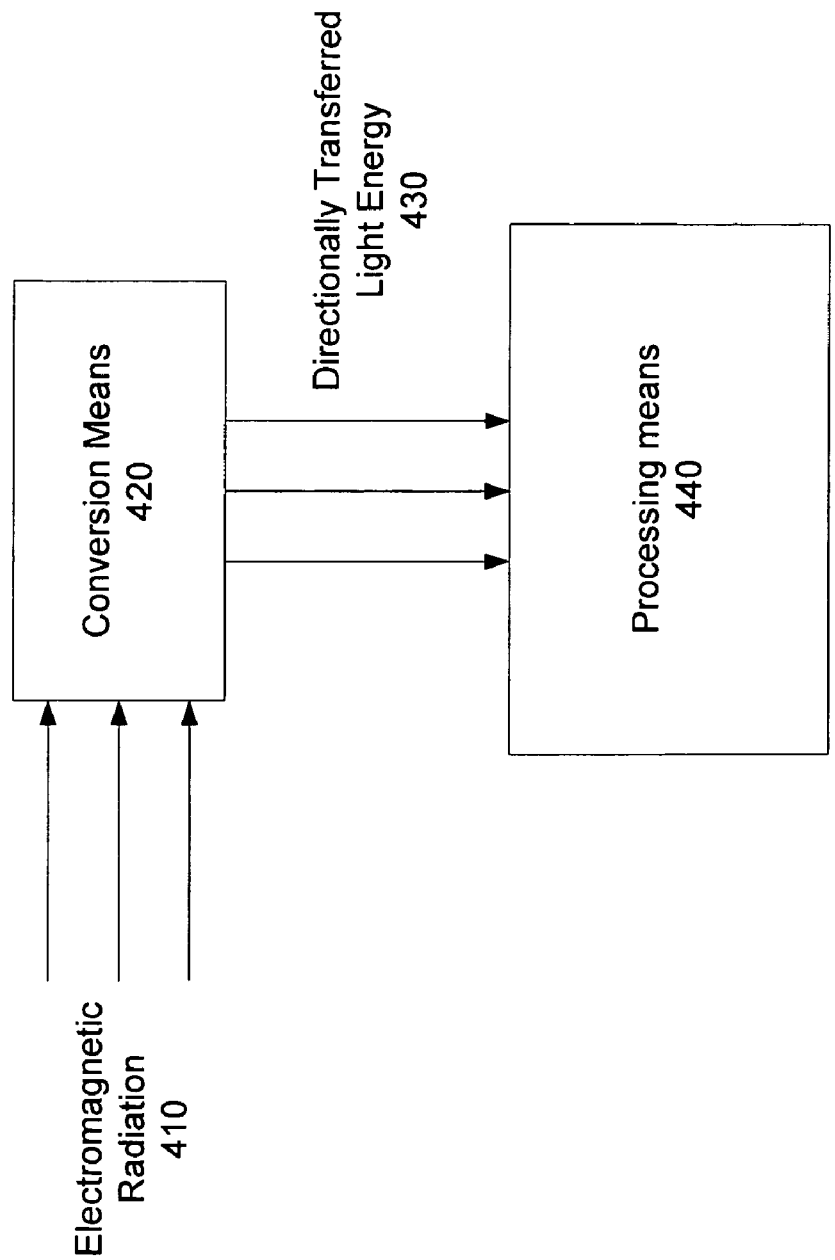
FIG. 4 shows conversion means 420 receiving electromagnetic radiation 410. The conversion means 420 may comprise a phycobilisome. The electromagnetic radiation 410 may comprise ultraviolet or visible light. The conversion means 420 may pass directionally transferred light energy 430 (e.g., red-shifted light energy) to processing means 440. Processing means 440 may comprise an optical fiber, photosensor, phycobilisome, waveguide, and/or optoelectronic device.
Figure 5:
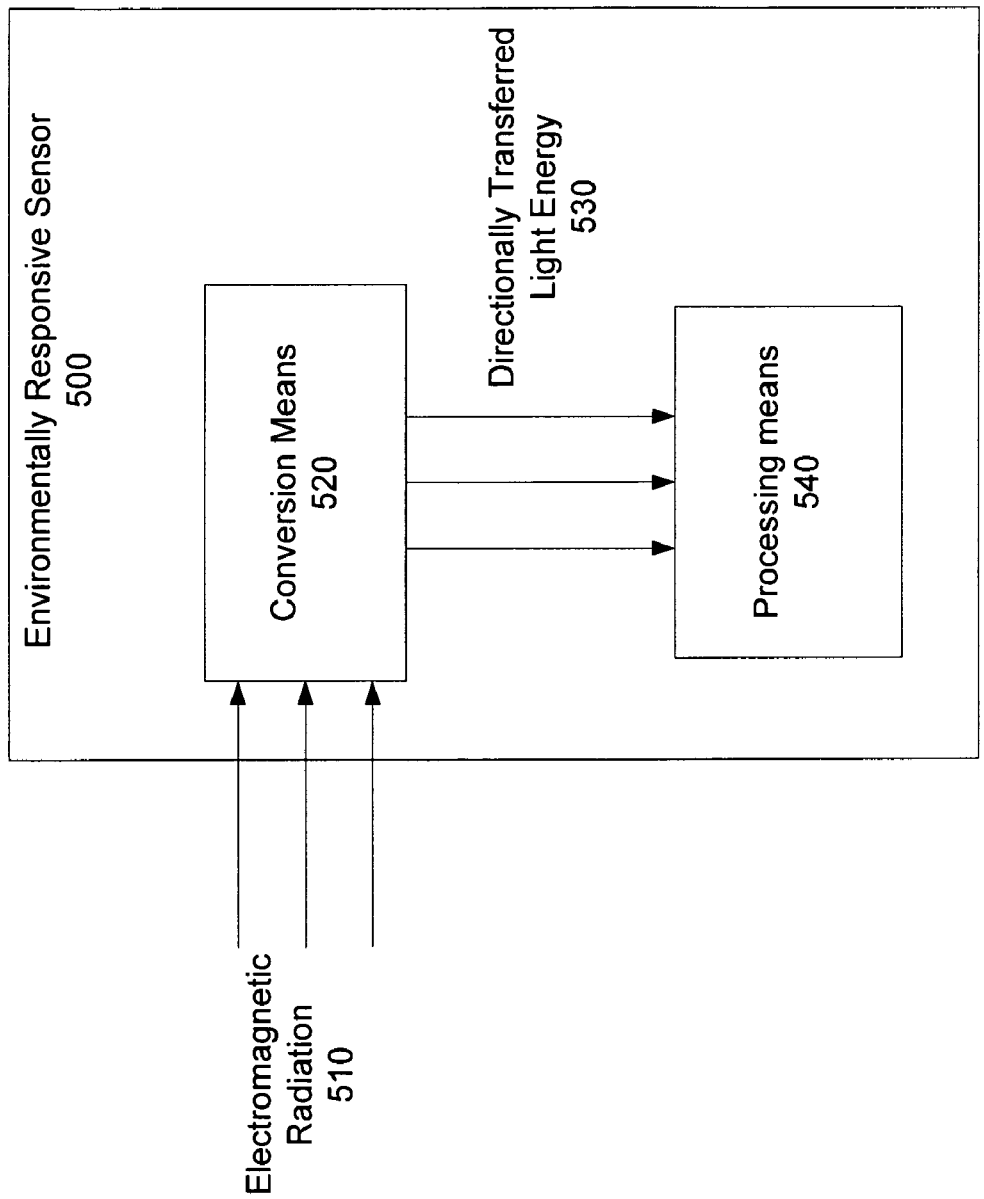
FIG. 5 shows an environmentally responsive sensor 500. The sensor 500 may comprise a conversion means 520 that receives electromagnetic radiation 510. The conversion means 520 may comprise a phycobilisome. The conversion means 520 may pass directionally transferred light energy to 530 to processing means 540.
Figure 6:
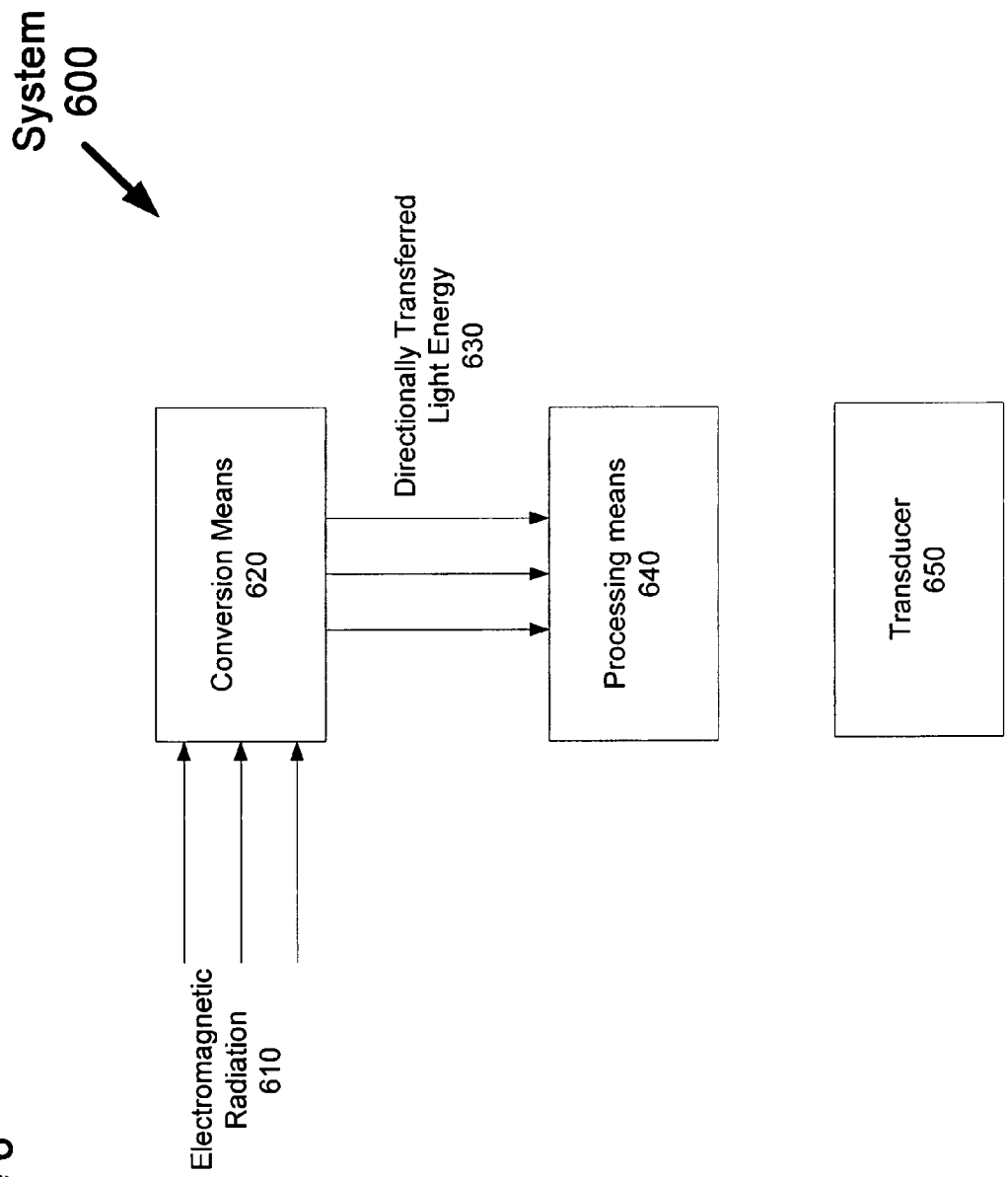

Phycobilisomes provide labels of high sensitivity due inter alia to their extremely large molecular weights, extinction coefficients, and energy transfer efficiencies, as well as to the high quantum yields of constituent phycobiliproteins. Directional energy transfer within phycobilisomes occurs from one or more "sensitizing species" to a terminal acceptor. A sensitizing species is a first fluorophor having an emission peak capable of exciting a second ("acceptor" or "emitter") fluorophor. Such energy transfer has application in homogeneous specific binding assays and in transducers comprising immobilized phycobilisomes.

It is a discovery of the present invention that phycobilisomes can be stabilized, conjugated, and/or modified so that they can be used intact in a variety of assays and formats. Among other things, this invention provides homogeneous preparations of isolated, soluble, stabilized phycobilisomes. Phycobilisomes may be isolated from the producing organisms after being stabilized in situ prior to cell disruption or in membrane-bound form following cell disruption. Alternatively, phycobilisomes may be isolated intact prior to in vitro stabilization or conjugation or immobilization. In yet another mode of operation, phycobiliproteins and linker proteins can be isolated and reconstituted in vitro to form phycobilisomes.

Phycobilisomes and phycobilisome complexes of the invention may be structurally stabilized to ensure that constituent phycobiliproteins, linker polypeptides and specifically bound components remain physically attached to one another throughout preparation and use. For applications requiring intra-phycobilisome energy transfer among constituent phycobiliproteins, this invention provides internally coupled phycobilisomes, prepared by stabilization methods that preserve inter-subunit energy transfer. Such internally coupled phycobilisomes may be detected by fluorescent, optoelectronic, piezoelectric, photometric, spectroscopic or visual means, among others. Structurally stabilized phycobilisomes which are not internally coupled are still useful as labels in specific binding assays, even though they do not provide the large Stokes shift, directional energy transfer or extraordinary fluorescence intensity of internally coupled phycobilisomes. Uncoupled phycobilisomes are primarily used as labels in fluorescent, photometric, spectroscopic, piezoelectric or visual-read assays or, alternatively, as high molecular weight scaffolds for attachment of signal-generating molecules (e.g., enzymes, fluorophores, luminescent or electroactive compounds) that can be detected by alternative (e.g., enzymatic, fluorescent, luminescent, optoelectric or electrochemical) means.

Definitions

The term "phycobilisome" as used herein means a supramolecular light-absorbing structure comprising at least one phycobiliprotein-containing rod and includes phycobilisomes; phycobilisome subassemblies; rod or core fractions; uncoupled, functionally altered or damaged phycobilisomes; genetically, physically, environmentally or chemically modified phycobilisomes; chromatically adapted phycobilisomes; isolated or partially isolated phycobilisomes; dissociated or partially dissociated phycobilisomes; reconstituted or rearranged or recombinant or hybrid phycobilisomes. Phycobilisomes as contemplated by the present invention contain two or more phycobiliproteins specifically connected by one or more linker polypeptides, where the two or more phycobiliproteins are in a particular orientation dictated by the linker polypeptide, with the orientation typically facilitating energy transfer between the phycobiliproteins. The "linker polypeptides" affect the phycobilisomes in a number of ways. First, phycobilisome linker polypeptides can determine the aggregation state and geometry of the particular biliproteins with which they interact. Second, they modulate the spectroscopic properties of the biliprotein. Third, they determine the location of the biliprotein within the phycobilisome and bridge between the biliprotein subcomplexes within the intact structure. In other words, linker polypeptides are proteins which bind two phycobiliproteins specifically and, upon binding, orient the phycobiliprotiens to enhance energy transfer between them. Linker polypeptides also dictate the defined and reproduce able supramolecular composition of phycobilisomes, as distinct, for example, from chemically cross-linked fluorescent polymers of fluorescent proteins. In addition, a large linker polypeptide may participate both in the assembly of the phycobilisome and in the attachment of the phycobilisome to the photosynthetic membrane.

Under appropriate conditions (e.g., high ionic strength), a mixture of isolated phycobiliproteins and linker polypeptides will form supramolecular structures analogous to those of naturally-occurring photosynthetic systems. Such complex structures form as a result of self-assembly directed by the linker polypeptides. Different linker polypeptides determine the composition of the phycobilisome, allowing self-assembly of multiple hexamers into a phycobilisome via the linker polypeptides. Typical structures created by this self-assembly will be one or more peripheral rods, or a phycobilisome core complex, or a complex of phycobiliproteins and core complex, connected by linker polypeptide(s). These self-assembled structures, or molecular entities having the same structure obtained by other means, are phycobilisomes as contemplated herein.

As used herein, the term "rod" means a peripheral rod or core complex or disc-and-core-complex or combination or subassembly having at least two discs joined by at least one linker polypeptide or at least one disc joined to a core complex by at least one linker polypeptide. Rods are known in the art to be stacks of multimeric phycobiliprotein discs joined by linker polypeptides (e.g., Glazer (1985a)). The term "disc" as used herein means a multimeric phycobiliprotein assemblage that can be reconstituted in vitro from isolated phycobiliprotein subunits (Grossman et al. (1993)). Such discs are typically either trimeric (single disc) or hexameric (double disc) and can be interconverted in vitro under suitable conditions (e.g., Glazer et al. (1971)). The core complex of a phycobilisome typically comprises at least two hexameric discs and associated linker polypeptides. Phycobilisomes of the instant invention, comprising at least one rod which comprises at least two discs, preferably share the common property of directional energy transfer, also referred to herein as "sidedness."

Phycobilisomes of the instant invention can be distinguished from isolated phycobiliproteins on structural criteria. Structurally, a phycobilisome comprises at least two hexamers (3 alpha and 3 beta subunits each) of a phycobiliprotein or phycobiliproteins joined by at least one linker polypeptide. While the phycobiliproteins R-PE and B-PE contain a gamma subunit (denoted a "linker" by some authors), isolated R-PE and B-PE are each distinguishable from a phycobilisome in that they are not connected to a second hexamer through a linker polypeptide. However, when two R-PE or two B-PE hexamers are linked by the gamma subunit in the orientation found between these two phycobiliportiens in nature, the resulting rod-like supramolecular entity may be considered a phycobilisome as the term is used herein. Phycobilsomes as contemplated by this invention are also distinct from compositionally and architecturally heterogeneous conjugates that have been prepared by covalently cross-linking isolated phycobiliproteins and other polypeptides.

While most rods in native phycobilisomes are stacks of three or four phycobiliprotein hexameric discs, this invention also contemplates rods with as few as two discs connected by linker polypeptide(s). The phycobilisome core complex is made up of the phycobiliprotein allophycocyanin (APC). Phycobiliproteins of the core form rods containing APC which contain other linker(s) and/or modified subunits. Examples of possible phycobilisomes, as defined under the instant invention, are APC linked to APC via linker polypeptides, APC linked to PC via linker polypeptides and PE linked to PC via linker polypeptides. Larger complexes containing additional phycobiliproteins remain within the definition of phycobilisomes, so long as the complex contains at least two phycobiliproteins which are linked and positioned in the complex by a linker polypeptide. Preferably, phycobilisomes of this invention will have at least three phycobiliprotein hexamers, and more preferably, the phycobilisomes of this invention will have at least the number of phycobiliproteins found in a single rod in nature or in the core complex.

"Stabilized phycobilisomes" are stable even under conditions of dilute ionic strength (<0.5 M) and protein concentration (<1 mg/ml), in contrast with native phycobilisomes. In addition, they are stable in the presence of glycerol, sucrose, and polyethylene glycol. Typically, the phycobilisomes are stabilized by means of a gentle crosslinking treatment, such as with formaldehyde or very low concentrations of glutaraldehyde. Other medium-, short- or zero-length crosslinking reagents may also be used.

Stabilized phycobilisomes that resist dissociation in dilute solution (<1 mg/ml protein) and low ionic strength buffers (<0.5 M) but are not energetically coupled (i.e., do not exhibit intra-phycobilisome energy transfer) may be used for embodiments of the invention which do not require internal energy transfer (i.e., internal coupling) between constituent phycobiliproteins, such as fluorescent, photometric or visual-read specific binding assays relying on the high molar extinction coefficient of phycobilisome labels. Excitation of the sensitizing phycobiliproteins of a structurally stabilized, energetically uncoupled phycobilisome does not lead to a major emission peak by the terminal acceptor. Stabilized phycobilisomes which retain the property of inter-phycobiliprotein energy transfer, by contrast, are referred to as "internally coupled phycobilisomes" and considered to be "functionally intact." Phycobilisomes which are functionally intact have a major emission peak at the wavelength of the terminal acceptor.

It will be understood to those of skill in the art that the extremely effective and efficient light-harvesting properties of internally coupled phycobilisomes provide distinct advantages for applications requiring highly sensitive detection and/or efficient signal transduction. It will also be apparent to the skilled artisan from the instant disclosure that structurally stabilized phycobilisomes which are internally uncoupled are suitable for certain applications described herein (e.g., Assay Example 1 (photometric immunoassay); Assay Example 5 (visual microliter immunoassay); and Assay Example 6 (immunochromatographic dipstick)). Other applications involving energy transduction and/or biotransducers (e.g., Energy Transduction Examples 1 and 2), may use either phycobilisomes that are internally coupled or, alternatively, structurally stabilized, internally uncoupled phycobilisomes which are conjugated to other molecular species (e.g., signal-generating molecules.)

"Isolated phycobilisomes" according to this invention are phycobilisomes that are not complexed to an intact thylakoid membrane. Phycobilisomes may be solubilized from thylakoid membranes by treatment with surfactants, detergents, lipids, phospholipids and other amphipathic molecules well-known in the art. Isolated phycobilisomes may be complexed to photosystem complexes which may in turn contain a thylakoid fragment, but when the isolated phycobilisomes of this invention are complexed to membrane structures, the membrane structures differ from naturally occurring thylakoid membranes in at least one characteristic. Typically a membrane-bound isolated phycobilisome will be complexed to a membrane structure that has been physically or chemically disrupted, e.g., by sonication or detergent treatment. Preferably, isolated phycobilisomes are stabilized, so that the phycobilisome resists dissociation in solutions of low ionic strength.

"Homogeneous preparations of isolated, soluble, stabilized phycobilisomes" according to this invention demonstrate homogeneity by lack of settling within a 24-hour incubation at 1×g. Solubility can be assessed by centrifugation. "Soluble phycobilisome preparation" means that upon centrifugation at 1,000×g for 5 minutes, greater than 55% of the phycobilisomes remain in the supernatant. It is desirable that greater than 65%, 75%, 85%, and even 90% of the phycobilisomes remain in the supernatant after such centrifugation, and such levels are possible using the methods of the present invention.

For the purpose of this invention, a "phycobilisome complex" is a supramolecular species of defined composition containing at least one isolated phycobilisome as defined above, the isolated phycobilisome further being specifically bound to at least one additional component. Typically, a phycobilisome complex will include more than one additional component, and may contain more than one phycobilisome. The term phycobilisome complex includes phycobilisome complexes containing, attached to, or capable of attaching to a second photosynthetic structure (e.g., an anchor polypeptide, a reaction center, a photosystem, a light-harvesting complex, a membrane protein or a membrane lipid). Further, a molecular species, which may be a ligand, a receptor or a signal-generating species, can be conjugated to the second photosynthetic structure. For example, photosystem II may be part of a phycobilisome complex and also serve as a site for conjugation of a ligand, receptor or signal-generating molecule.

The phycobilisome complex may or may not be soluble. Stabilized phycobilisome complexes comprising thylakoid membrane-associated constituents (e.g., a reaction center, photosystem light-harvesting complex, membrane protein or membrane lipid) may be insoluble in aqueous buffers and may be solubilized by treatment with surfactants, detergents, lipids, phospholipids and other amphipathic molecules well-known in the art. A phycobilisome complex may also be immobilized to a manufactured solid support.

The term "ligand" means any substance capable of specifically binding to a receptor. Ligands include but are not limited to agonists, antagonists, biotin (or derivatives, such as amino-biotin, imino-biotin, and diamino-biotin), haptens, antigens, carbohydrates, drugs, hormones, transmitters, cofactors, vitamins, toxins, oligonucleotides, nucleic acids, aptamers, and conjugates formed by attaching any of these molecules to a second molecule. The term "receptor" means any substance capable of specifically binding to a ligand. Receptors include but are not limited to antibodies, antibody fragments, antibody mimetics, molecular mimics and molecular imprints, molecular recognition units, adhesion molecules, soluble receptors, avidin, streptavidin, lectins, selectins, oligonucleotides, nucleic acids, membrane receptors, cellular receptors, and drug receptors. The terms "specifically bind," "specifically bound" and "specific binding" refer to the saturable, noncovalent interaction between a ligand and a receptor which is well known in the art and explicitly includes nucleic acid hybridization. "Hybridization" refers to specific binding between two or more nucleic acid sequences through complementary base pairing. Such binding is also referred to as Watson-Crick base pairing. For hybridization, a sufficient degree of complementarity is required to yield reversible binding between two selected nucleic acid sequences. Perfect complementarity is not required and may not be preferred for embodiments relying on reversibility, such as dissociation of a hybridized nucleic acid probe reagent by a target sequence.

"Signal-generating molecule" as used herein means any substance capable of generating a detectable signal or enhancing or modulating the detectability of a phycobilisome or transducing a phycobilisome signal into a qualitatively or quantitatively different signal or different form of energy. "Enhancing or modulating phycobilisome detectability" means the signal-generating molecule has an effect on phycobilisome size, shape, charge, chemical composition or spectral properties or that the phycobilisome-signal-generating molecule conjugate has different spectral properties from the unconjugated phycobilisome. "Transducing the phycobilisome signal" means the conjugate absorbs or emits in a different region of the electromagnetic spectrum from the unconjugated phycobilisome or the conjugate manifests an energy or function different from the unconjugated phycobilisome, such as an electric or chemical potential or catalytic activity or thermal gradient or mechanical force. Signal-generating molecules as contemplated herein include, but are not limited to, signal-generating systems comprising phycobiliproteins, dye molecules, colloids, fluorophores and other photoactive molecules, enzymes, coenzymes, cofactors, catalytic antibodies, ribozymes, and other catalytic molecules, molecular mimics, luminescent compounds, oxidizing and reducing compounds and other electroactive molecules, photosystem molecules and reaction centers not attached to phycobilisomes in nature such as artificial reaction centers, optionally including organizational, scaffold and coupling molecules used to capture energy in artificial photosynthesis, and even other phycobilisomes.

"Molecular mimics" and "mimetics" are synthetic molecules or groups of molecules designed or selected to perform an equivalent or similar function to that of a naturally occurring or biological molecule or group of molecules. "Artificial photosynthesis" refers to synthetic energy conversion systems that mimic the natural process of photosynthesis. "Artificial reaction center" means a molecule or group of molecules capable of existing in a light-induced charge-separated state, thereby mimicking the function of a reaction center. Examples of artificial reaction centers are well-known in the art (Gust, et al. (1993), "Molecular mimicry of photosynthetic energy and electron trasfer," *Accounts of Chemical Research*, 26:198–205; Gust, et al. (1994), "Photosynthesis mimics as molecular electronic devices," *IEEE. Eng. Med. Biol.*, 13:58–66, and references therein). "Reaction center" means a natural photosynthetic molecule or group of molecules in which photoinitiated electron transfer culminates in a relatively long-lived, charge-separated state. The term "photosystem" as used herein means a photosynthetic molecule or group of molecules that serves as a functionally coupled energy transfer acceptor from a reaction center, for example, photosystem I or photosystem II.

"Light energy" as defined herein is a discrete energy packet that was originally resident in a photon; light energy as contemplated herein may be transformed into other energy forms. Typically, the photon (and its light energy) will be absorbed by a pigmented substance. The light energy from the photon may be subsequently transferred from the absorbing species radiatively by photon emission, or the light energy may be non-radiatively transferred to an acceptor species.

Efficient signal or energy transduction (i.e., transfer of light energy) between a phycobilisome and an attached signal-generating molecule requires functional coupling between the two species. "Functional coupling" means that two processes are connected by a common intermediate or that two species or substances participate as donor and acceptor in the transfer of mass or energy, e.g., photons or electrons or chemical or mechanical or thermal energy. The term "functionally coupled" means that a first species, substance or process is connected to a second species, substance or process by a common intermediate or by transfer of a photon, electron, property, activity, mass or energy from a donor to an acceptor. Such coupling is well known in the art (Cubicciotti, R. (1993) DNA chips. "Medical & Healthcare Marketplace Guide." *MLR Biomedical Information Services, 9th Edition*, pp. 113–115; Cubicciotti, R. S. (1995) "Nucleotide-directed assembly of bimolecular and multimolecular drugs and devices." WIPO International Publication No. WO 95/16788, p. 24; Gust et al. (1993), Sheeler, P. and Bianchi, D E (1983) "Cell Biology: Structure, Biochemistry, and Function", p. 203, John Wiley & Sons, Inc., New York; Saier, H S Jr. (1987), "Enzymes in Metabolic Pathways: A comparative Study of Mechanism, Structure, Evolution, and Control", pp. 48–59 and 132–136, Harper & Row Publishers, New York; Aidley D. J. (1989), *The Physiology of Excitable Cells*, Third Edition, p. 320, Cambridge University Press, Cambridge; Bray, HG and White, K (1957); *Kinetics and Thermodynamics in Biochemistry*, p. 135, Academic Press, New York; and Guyton, A C (1971) *Textbook of Medical Physiology*, Fourth Edition, p. 786, W. B. Saunders Company, Philadelphia). Examples of such coupling are described by Cubicciotti (1995) to include, for example:

. . . coupling proteins to selectively or actively transport ions and metabolites; coupling cytochromes to transduce chemical energy by means of electron transfer-dependent oxidation-reduction reactions; coupling redox mediators such as ubiquinones, ferricinium salts, rubidium, viologens, tetrathiofulvalene, tetracyanoquinidodimethane, N-methylphenazinium, benzoquinone or conducting polymers or organic conducting salts to transfer electrons between electroactive molecules such as redox enzymes and electrodes in bioelectronic and optoelectronic devices such as biosensors and biochips; coupling photoactive compounds such as fluorophores with other photoactive compounds or with redox proteins or enzymes for energy transfer devices and artificial photosynthetic systems; and coupling pro-drugs for staged-delivery or triggered activation.

Phycobilisomes are said to be functionally coupled to a second molecular species or a device (e.g., a transducer) when a photon, electron, property, activity, mass or energy of a first molecule, complex or device comprising the phycobilisome is transferred to or from a second molecule, complex or device. For certain functionally coupled conjugate and biotransducer embodiments, particularly those involving phycobilisomes, artificial reaction centers and electronic transducers, electronic coupling is preferred. "Electronic coupling" as used herein includes single-electron transfer and coupling mediated by direct, through-space overlap of the relevant orbitals of the donor(s) and acceptor and by through-bond superexchange(s) and may occur by single-step or multistep processes within a molecule or between molecules positioned by covalent bonding or non-covalent interaction(s).

Based on the foregoing definitions, it will be apparent to one of skill in the art that a ligand, receptor or signal-generating molecule attached to a phycobilisome can further be functionally coupled to the phycobilisome, and that functional coupling includes the exchange or transfer of mass or energy between a phycobilisome and an attached species. Functional coupling does not require direct attachment of a signal-generating molecule to a phycobilisome. A phycobilisome can be functionally coupled to a second molecule or complex or device or process indirectly, e.g., through a specific binding reaction between an attached ligand or receptor and a specific binding partner comprising a signal-generating molecule.

The term "manufactured solid support" as used herein means any structure, device, matrix or membrane which is not the native attachment site for phycobilisomes and includes non-thylakoid biological membranes and synthetic and biomimetic membranes which may comprise peptides, proteins and/or other ligands and receptors. Non-thylakoid, synthetic and biomimetic membranes can either be used directly as solid supports, or attached to or deposited or prepared on solid supports, to facilitate self-assembly, reconstitution and/or immobilization of phycobilisomes, phycobilisome subassemblies and conjugates via covalent or non-covalent attachment. In addition, phycobilisome complexes of the invention comprising thylakoid membrane fragments or constituents (e.g., lipids, proteins and membrane receptors) may be immobilized to a manufactured solid support.

The term "biotransducer" as used herein means biological or biomimetic molecule(s) immobilized at and/or functionally coupled to a transducer. "Biological or biomimetic"

molecule(s) may be isolated from biological sources or produced synthetically or may perform a function equivalent to biological molecule(s), e.g., immunologic recognition, nucleic acid hybridization, enzymatic catalysis, photosynthesis or a component reaction of photosynthesis. "Phycobilisome-based biotransducer" means a biotransducer comprising a phycobilisome or phycobilisome complex, wherein the phycobilisome and transducer elements are necessary and functionally inseparable components of a product or system which performs a useful function. Where an instrument or device (e.g., a microscope, fluorometer, spectrofluorometer or Clark electrode) merely performs the function of measuring a property or activity of a phycobilisome or phycobilisome preparation (e.g., size, fluorescence, absorbance or rate of oxygen evolution), the instrument is not a phycobilisome-based biotransducer, because the phycobilisome is not a component of the measuring device. Instead, in such an instance the phycobilisome or phycobilisome preparation is the object of measurement or the sample to be measured and is both structurally and functionally unnecessary to and separable from the product that performs the measurement. By contrast, the phycobilisome of a phycobilisome-based biotransducer is operatively associated with, attached to, immobilized at, packaged with, or otherwise structurally or functionally inseparable from the transducer. A phycobilisome-based biotransducer can, of course, be a two-component (or multi-component) product or system comprising a transducer component and a disposable, replaceable, reusable or upgradeable phycobilisome-containing cartridge, module, slide, disk, film, layer, fiber, connector, attachment or part that serves as an interface between the phycobilisome and the transducer. In such a case, the phycobilisome-containing component is physically separable from the transducer component but must be inserted, attached, rejoined or replaced to form the functionally coupled two-component system capable of performing the intended function. The "functionally coupled" transducer converts an activity, energy or property of the biological or biomimetic molecule(s) (e.g., the phycobilisome(s) or phycobilisome conjugate(s)) to useful work or information or a detectable signal.

Preparation of Modified Phycobilisomes

Phycobilisome Isolation

Phycobilisomes, according to the present invention, are self-assembling complexes of phycobiliproteins and linker proteins comprising at least one rod. The phycobilisomes of the present invention may be obtained from either prokaryotic cyanobacteria (blue-green algae) or eukaryotic red algae. The algae may be wild-type, mutants, hybrids, or genetic recombinants capable of expressing phycobilisome constituents. The algae may be harvested from natural environments (the wild) or grown under artificially controlled conditions. Such artificial conditions may simulate a natural environment or they may be designed to induce chromatic adaption, for example, to modulate the composition of phycobilisomes. Artificial conditions may support either autotrophic, mixotrophic, or heterotrophic growth.

General procedures for isolation of phycobilisomes from a wide range of unicellular algae have been described (see, e.g., Gantt et al. (1979) *Plant Physiol.* 63:615–620). Phycobilisomes can be isolated from red algae (e.g., *Porphyridium cruentum*) and blue-green algae (e.g., *Anabaena variabilis, Spirulina platensis*) by methods modified from those of Gantt and Lipschultz (1972) *J. Cell Biol.* 54:313–324. Typically, algal or cyanobacterial cells grown under conditions which elicit production of the photosynthetic apparatus in the cells are lysed in a phosphate buffered detergent solution. After removing cellular debris, phycobilisomes may be isolated from the aqueous supernatant by gradient centrifugation or precipitation with high concentrations of phosphate buffer ($\leq 1$ M) or polyols (e.g., sucrose or polyethylene glycol). Isolated phycobilisomes are redissolved in phosphate buffer (about 0.75M). Exemplary procedures are shown below.

Exemplary Procedure 1. Isolation of Phycobilisomes from Red and Blue-green Algae by Gradient Ultracentrifugation Freshly cultured or frozen (−20° C. or −70° C.) algae can be cultured autotrophically in 40–500 L stirred tanks with continuous fluorescent illumination and harvested by centrifugation. *Porphyridium cruentum* (*P. cruentum*) can be grown at 20–22° C. in an artificial seawater medium (pH 8.0) comprising sodium salts, Tadros Metals, Instant Ocean and Dunaliella vitamins. *Anabaena variabilis* can be grown at 25° C. in double-strength BG-11 medium containing sodium and potassium salts, magnesium sulfate, calcium chloride, citric acid, ferric ammonium citrate and A5 Metals (pH 7.8).

Unless otherwise specified, all preparative steps can be performed at room temperature (20–23° C.) in 0.75 M potassium phosphate (pH 7.0–7.2) optionally containing 0.05% sodium azide (KPi buffer). Twenty-four grams (wet weight) of packed cells are resuspended in 48 ml KPi buffer. PMSF (1 mM), benzamidine (5 mM) and DNase I (10 ul of RNase-free stock at 10 U/ul) are then added, and the suspension is passed four times in 15 ml increments through a French pressure cell (Aminco) operated at 1000–1250 p.s.i. TRITON X-100 (t-octylphenoxypolyethoxyethanol, Rohm and Haas) is added to 2% and the broken cell mixture is stirred for 20 minutes. Particulate matter is removed by centrifugation at 15,000 rpm for 45 minutes in a Sorvall RC-5B Refrigerated Superspeed Centrifuge using an SS34 rotor. The supernatant is withdrawn by syringe from underneath the floating chlorophyll fraction, and approximately 9 ml is layered on each of six buffered sucrose step gradients comprising (from bottom to top) 2 M sucrose (4 ml), 1 M sucrose (8 ml), 0.5 M sucrose (7 ml) and 0.25 M sucrose (7 ml), all in 0.75 M KPi. Gradients are centrifuged 12–18 hours at 25,000 rpm in an SW27 rotor. Following centrifugation, green, brown, brown-red, purple-red, purple and clear layers (top to bottom) can be discerned with varying resolution. Only the purple-red (rods and phycobiliprotein aggregates) and purple (phycobilisome) bands are retained. Purple-red bands are withdrawn by suction using a pasteur pipet, pooled and stored at 2–8° C. Stabilized and conjugated rods may be prepared from this fraction, purified by gel chromatography, and immobilized. Purple phycobilisome bands in the 1.0 M sucrose layer are withdrawn, pooled, diluted four-fold with KPi buffer and centrifuged at 15,000 rpm for 40 minutes in an SS34 rotor. Resultant supernatants are withdrawn from pelleted sediment (if any) and centrifuged at 30,000 rpm for two hours in a VTi50 rotor. Final supernatants are quickly and carefully aspirated, and phycobilisome-containing pellets are resuspended in a minimal volume of KPi buffer. Protein concentration can be determined by the method of Lowry et al. (1951 *J. Biol. Chem.*, 193:265–275). Protein measurements are carried out with the Folin phenol reagent using bovine serum albumin as standard with suitable controls for sucrose and TRITON X-100 interference. Absorption spectra were measured with a Shimadzu Model UV-160 recording spectrophotometer. Fluorescence spectra were recorded at room temperature in a 4 ml quartz cuvette with a SPEX FLUOROMAX™ (scanning excitation/emission fluorometer) coupled to a Compudyne PC.

In general, phycobilisome emission spectra can be obtained by exciting phycobilisomes using fight of wavelengths within the absorption spectrum of the distal sensitizing phycobiliprotein (e.g., 545 nm for *P. cruentum* B-PE). Phycobilisomes can be routinely characterized by 1) peak absorption per mg protein (e.g., $AU_{545}$/mg for *P. cruentum*), 2) fluorescence signal per defined concentration (e.g., cps at Emax for intact phycobilisomes at 10 ng/ml), and 3) one or more fluorescence ratios reflecting the efficiency of inter-phycobiliprotein energy transfer (e.g., 666/573 nm emission for *P. cruentum* as an index of APC/B-PE coupling). Up to 24 grams wet weight of biomass can be conveniently handled using six 35 ml centrifuge tubes in an SW27 rotor for the final sucrose gradient ultracentrifugation step. Phycobilisome recovery is on the order of 0.1–1.0% of initial biomass.

Exemplary Procedure 2. Large-scale Isolation of Phycobilisomes Without Gradient Ultracentrifugation The convenience, scale and cost-effectiveness of phycobilisome isolation by conventional methods (e.g., Gantt and Lipschultz (1972) supra, Gantt et al. (1979) supra) are severely limited by the need for gradient ultracentrifugation. To enable scalable and economical production of phycobilisomes, procedures were developed for isolating phycobilisomes from different organisms without gradient ultracentrifugation. Methods based on those for *Anabaena variabilis* using TRITON X-100 solubilization and PEG precipitation failed to yield intact phycobilisomes from some organisms, notably *P. cruentum*. An additional treatment step is required to protect *P. cruentum* phycobilisomes during removal of Triton X-100 and PEG. Either sucrose or formaldehyde treatment was found to be effective. Summarized below is the sucrose treatment procedure, which has been validated with modification for both rhodophytes (e.g., *P. cruentum*) and cyanophytes (e.g., *Anabaena variabilis, Spirulina platensis*). Preparative scale can be readily varied by selecting different centrifuge and rotor combinations and adjusting volumes accordingly.

Cells are suspended in 5 ml 0.75 M KPi (pH 6.8) per gram wet weight. PMSF and benzamidine are added to a final concentration of 1 mM and 5 mM, respectively, and the suspension is passed through a French pressure cell three times at 1000–1250 p.s.i. Membrane-associated phycobilisomes are solubilized by treatment with 2% TRITON X-100 in 0.75 M KPi (pH 6.8) for 20 minutes with stirring. The broken cell preparation is centrifuged at 15,000 rpm for 20 minutes in a Sorvall RC-5B Refrigerated Superspeed Centrifuge using an SS34 rotor to remove membrane fragments and particulate debris. The supernatant is collected by suction from underneath the floating chlorophyll layer. The pellet is discarded. Polyethylene glycol 8000 is added to the supernatant to a concentration of 15% (wt/vol). The mixture is stirred for one hour and centrifuged for 20 minutes at 15,000 rpm in an SS34 rotor. The supernatant is discarded. The pellet is resuspended by addition of 2 M sucrose in 0.75 M KPi with gentle vortexing to a final concentration of 1.5 M sucrose. Thirty minutes following sucrose addition, the suspension is diluted approximately 4-fold with 0.75 M KPi (pH 6.8) and centrifuged for three hours at 40,000 rpm (20° C.) in a Beckman L8-M Ultracentrifuge using a VTi50 rotor. The supernatant is discarded. The pellet is resuspended in a minimal volume of 0.75 M KPi (pH 6.8), characterized by protein, absorption and fluorescence measurements (cf. supra) and stored either refrigerated or at ambient temperature, depending on the source of phycobilisomes.

Exemplary Procedure 3. Large-scale Preparation of Phycobilisomes from Algae

An alternative large-scale isolation procedure described by Grossman and Brand (1983, Carnegie Institution of Washington Yearbook, 82, 116–120) can also be used to prepare phycobilisomes. While this procedure has not been widely used due to the requirement for large-scale preparative centrifugation, it can be adapted to a suitable scale using appropriately sized centrifuge tubes. This procedure, called the "rapid pelleting method" by the authors, involves breaking the cells in 1 M phosphate buffer by passing cells through a French pressure cell. The lysate is brought to 1% TRITON X-100, incubated at room temperature for 30 min, then centrifuged at 32,000×g for 30 min. With laboratory scale preparative centrifuges (e.g., Sorval RC-5A), this is done in very small centrifuge tubes (e.g., using the SS34 rotor the tubes are about 45 mL with 8 places giving about 300 mL useful volume per centrifugation run). The pellet is resuspended in 0.6 M phosphate buffer (pH 7.5) and homogenized in a glass homogenizer. TRITON X-100 is added to 1% and incubated for 30 min at room temperature. The solution is again centrifuged at 32,000×g for 30 min. A large amount of the phycobilisome then remains in solution, so the pellet is discarded. The supernatant is diluted 10-fold with 1.0 M $NaKPO_4$ (pH 7.5) and centrifuged at 32,000×g for 1 h to bring down the phycobilisomes. This method has been applied to various algal phycobilisomes (e.g., *Anacystis nidulans, Porphyridium aerugineum, Cyanidium caldarium*) from a diverse group of algae (Grossman and Brand (1983) Carnegie Institution of Washington Yearbook 82, 116–120) and can be adapted for phycobilisome preparation from many species.

Exemplary Procedure 4. Preparation of Phycobilisomes from Cyanobacteria

Another alternative isolation procedure has been described for preparation of cyanobacterial phycobilisomes (Siegelman and Kycia (1982) *Plant Physiol.*, 70:887–897). Phycobilisomes containing phycoerythrin can be isolated in the following way. Cells are lysed in a 1.0 M potassium phosphate buffer (pH 6.8) containing 1% TRITON X-100 by stirring for 1 to 1.5 h at room temperature. The suspension is centrifuged at low speed and the supernatant discarded. The pellet is resuspended in 0.5 M potassium phosphate (pH 6.8) containing 1% TRITON X-100 and centrifuged for 5 min. The supernatant containing the phycobilisomes is removed so that the chlorophyll fraction is left in the tube. The solubilized phycobilisomes are precipitated by addition of solid potassium phosphate (at a 1:1 ratio of dibasic and monobasic forms) to a final concentration of 1.5 M at pH 6.8. This is centrifuged for 10 min and the clear supernatant removed from the soft pellet containing the phycobilisomes. The phycobilisome pellet is suspended in 0.5 M potassium phosphate (pH 6.8) with 1% TRITON X-100 and precipitated again. The twice precipitated phycobilisomes are resuspended in 1.25 M potassium phosphate (pH 6.8) and stored frozen. Phycobilisomes containing no phycoerythrin can also be isolated with minimal changes to the above procedure, the changes consisting essentially of increasing the amount of potassium phosphate used to precipitate the phycobilisomes from 1.0 M to 1.25 M in several of the steps. With other minimal modifications, this method may be applied to red algae such as *P. cruentum*.

Stabilization of Phycobilisomes

In agreement with published studies (e.g., Katoh (1988) Phycobilisome stability, in Methods in Enzymology Vol. 167, pp. 313–318, Academic Press; and Gantt et al., 1979, supra), isolated phycobilisomes were shown to be unstable to decreases in protein concentration and ionic strength. Using *P. cruentum* phycobilisomes, for example, intra-phycobilisome energy transfer was disrupted within minutes following dilution of protein (below about 1 mg/ml) or buffer (below about 0.5 M KPi), as exhibited by concentration-dependent decreases in the ratio of 666/573 nm fluorescence emission with 545 nm excitation. Similar dissociation was observed for phycobilisomes isolated from *Spirulina platensis* and *Anabaena variabilis* based on a decrease in emission of the terminal acceptor. To enable reproducible preparation of stable phycobilisome-labeled ligands and receptors for use in conventional specific binding assay configurations, phycobilisomes are preferably stabilized against dissociation.

Stabilization methods which are embraced by the present invention include covalent as well as non-covalent means. Covalent methods include crosslinking and multi-point attachment of polymers that span at least two phycobilisome constituent proteins. Crosslinking agents may be zero-length (involving the direct attachment of two phycobilisome groups without intervening spacer atoms) or they may include spacer arms of varying length. Non-covalent stabilization may be accomplished using cosolvents, such as salts and sugars, hydrophobic or affinity-based interactions, such as with certain polymers or polyvalent receptors, entrapment or encapsulation (e.g., using gels, liposomes, or micelles), or changes in physical state, such as freezing or dehydrating. Suitable methods for stabilizing phycobilisomes include the methods discussed below.

(1) Covalent stabilization can be accomplished by intra-phycobilisome (inter-subunit) crosslinking, preferably through use of short- or zero-length bifunctional reagents well-known in the art of protein modification (e.g., Wong (1991) *Chemistry of Protein Conjugation and Crosslinking*, CRC Press).

(2) Covalent stabilization can also be achieved by multi-site attachment of natural or synthetic polymers such as carbohydrates, lipids, oligonucleotides, proteins, peptides, polyamino acids, random or ordered copolymers of amino acids, nucleosides, sugars or other small organic molecules. This method for covalent interconnection of phycobilisome subunits can be performed using either one-step or two-step techniques. In the preferred two-step approach, a first reactant (either the phycobilisome or the bridging polymer) is activated in step one. Following removal of excess reagent, the activated reactant is attached in step two to functional groups on the second reactant.

(3) Non-covalent stabilization can be achieved using cosolvents, detergents or other buffer additives that render phycobilisome dissociation thermodynamically unfavorable. In a particular embodiment, phycobilisomes are encapsulated by sonication to form vesicles containing the phycobilisomes in a solution which promotes non-covalent stabilization (e.g., 0.75 M phosphate buffer). Suitable materials for formation of liposomes around a stabilizing solution of phycobilisomes may be readily selected by the skilled worker (see discussion of immobilization to liposomes below). Ligands or receptors or other suitable molecular species may be introduced into the liposome membrane, as is well known in the art, thereby conferring specific binding properties on the encapsulated phycobilisomes.

(4) Non-covalent, affinity-based stabilization can also be accomplished using molecules or groups of molecules having a finite affinity for functional binding sites spanning at least two phycobilisome subunits. Molecules having suitable affinity may be selected by screening or combinatorial methods from groups such as naturally occurring, modified or synthetic antibodies or antibody fragments, oligonucleotides, peptides, proteins, lectins, carbohydrates or polymers of small organic molecules. Affinity can be determined by binding studies, but suitable molecules may be more simply identified by monitoring intra-phycobilisome energy transfer upon dilution of the phycobiliprotein or buffer concentration.

Phycobilisomes may be isolated from the producing organisms after being stabilized in situ prior to cell disruption or in membrane-bound form following cell disruption. Alternatively, phycobilisomes may be isolated intact prior to in vitro stabilization or conjugation or immobilization. In yet another mode of operation, phycobiliproteins and linker proteins can be isolated and reconstituted in vitro to form phycobilisomes, which are then stabilized as described herein.

In a preferred embodiment, phycobilisomes can be stabilized through a one-step reaction with short to medium chain-length crosslinking agents. To produce stabilized phycobilisomes that remain soluble, reagents and reaction conditions are selected to favor intra-phycobilisome crosslinking over inter-phycobilisome polymerization. The medium chain-length homobifunctional dialdehyde, glutaraldehyde (GA), and the short chain-length monoaldehyde, formaldehyde (FA), are both effective in protecting phycobilisomes from dilution-induced uncoupling of energy transfer. Maximal stabilization of phycobilisomes with GA is accompanied by partial insolubilization which is only apparent following centrifugation or prolonged storage. GA-induced insolubilization can be minimized through co-optimization of GA and phycobilisome concentrations, pH, buffer concentration, and reaction time. Alternatively, conditions can be adjusted to yield GA-stabilized phycobilisomes that remain in homogeneous suspension, but sediment completely when centrifuged at 8000 g for two minutes. The stabilizing effect of GA can be improved by sequential treatment of phycobilisomes at low GA/phycobilisome mass ratio (e.g., 0.027% GA/0.727% phycobilisomes) followed by dilution of the reaction mixture with buffered GA to increase the GA/phycobilisome ratio (e.g., to 0.10% GA/0.10% phycobilisomes). In contrast to GA treatment, maximally effective stabilization with shorter chain-length crosslinkers (e.g., FA) can be achieved without loss of soluble phycobilisomes to aggregation or precipitation.

Isolated phycobilisomes, stabilized phycobilisomes and phycobilisome conjugates prepared from different cyanobacteria and rhodophytes were exposed to a diverse assortment of substances and conditions to identify chemical and environmental factors capable of modulating either the aggregation state or spectral properties of the different phycobilisome preparations. Phycobilisomes diluted to concentrations ranging from 10 ug/ml to 10 mg/ml were subjected to varying temperatures, pressures, freeze-thaw cycles, lyophilization conditions, light sources and exposures, mechanical shaking, sonication, ultracentrifugation, ultrafiltration, dialysis, electrophoresis, pH, ionic strength, buffers, acids, bases, chaotropic agents, sugars, salts, neutral and charged polymers, copolymers, ionic and nonionic detergents, polar and nonpolar solvents, oxidizing and reducing agents, protein modifying reagents and combinations of such treatments designed to reversibly modulate or irreversibly perturb the phycobilisome aggregation state or spectral properties. For all but the most extreme interventions (e.g., denaturing conditions), phycobilisome preparations could be identified with varying tolerances to each type of treatment, suggesting the possibility of using selected or engineered phycobilisomes to sense and report conditions in a particular environment or sample. Especially noteworthy were differences in phycobilisome fluorescent properties in dry and partially hydrated states as a function of stabilization and storage conditions.

STABILIZATION EXAMPLE 1

Cross-linked Phycobilisomes Tested for Functionality

To determine effects of stabilization and conjugation procedures on the size distribution and buoyant density of phycobilisome preparations, the behavior of reaction precursors and products was evaluated on discontinuous sucrose gradients similar to those used for phycobilisome isolation. One-half milligram aliquots of lysine-quenched, GA-stabilized phycobilisomes, unpurified phycobilisome-antibody conjugates and unmodified phycobilisomes were applied to 10 ml sucrose gradients comprising 2.5 ml steps of 2.0 M, 1.0 M, 0.5 M and 0.25 M sucrose in 0.75 M KPi (pH 7.35). Gradients were centrifuged 20 hours (18° C.) at 50,000 rpm in a 70.1 Ti rotor. A purple-red band (rods and B-PE aggregates) appeared in the upper half of the unmodified phycobilisome gradient, indicating some breakdown of native phycobilisomes under these conditions. GA-stabilized phycobilisomes and phycobilisome-antibody conjugate gradients, by contrast, formed a single band in the 1.5 M sucrose region. These results indicate that 1) GA treatment successfully prevented phycobilisome dissociation during ultracentrifugation, 2) the one-step GA stabilization/conjugation process did not yield uncontrolled polymerization of phycobilisomes or conjugates, and 3) stabilized phycobilisomes and conjugates remained soluble following covalent crosslinking by methods described herein.

STABILIZATION EXAMPLE 2

Preparation of a Stable, Modified Phycobilisome Reagent Using Formaldehyde

For most uses of phycobilisomes as detection reagents, it is preferred that they remain structurally intact ("non-dissociated"). For use in heterogeneous specific binding assays (in which bound and free labeled species must be separated prior to measurement), phycobilisomes are preferably stabilized to prevent spontaneous dissociation during conjugation, purification, assay, product manufacturing, shipping and storage. Covalent stabilization methods of this invention can preserve the energetic coupling and/or structural integrity of phycobilisomes without compromising solubility. Crosslinkers were used under conditions carefully optimized to avoid precipitation arising from uncontrolled polymerization or charge neutralization. Key optimization parameters included crosslinker type and reactivity, absolute and relative reagent and phycobilisome concentrations, reaction time, pH, and methods for termination and purification. Formaldehyde stabilization, exemplified using $P.$ $cruentum$ phycobilisomes, was performed as follows.

Isolated phycobilisomes were adjusted to a protein concentration of 8.0 mg/ml in 0.75 M KPi (pH 7.2) containing 0.05% sodium azide. FA (formaldehyde) (11% in 0.75 M KPi) was added dropwise with vortexing in a 10% volume to yield a final concentration of 1.0%. The reaction mixture was left standing for 18 hours at room temperature and quenched with 1 M L-lysine. For prolonged storage, FA-treated phycobilisomes were reduced with sodium cyanoborohydride and purified over SEPHAROSE CL-6B equilibrated with 100 mM KPi (pH 7.2) containing 150 mM sodium chloride and 0.05% sodium azide.

Phycobilisome susceptibility to dissociation following dilution was prevented by FA treatment in a time- and dose-dependent manner. Preparations treated at varying FA concentrations for 18 hours were incubated for two hours in 0.75 M KPi (pH 7.2) at 65 ug/ml and 0.6 ug/ml, respectively, prior to absorption and fluorescence measurements (545 nm excitation).

| [FA] (%) (×18 hr) | $AU_{545}$ (@65 ug/ml) | Fluorescence Emission (@0.6 ug/ml) | | Ratio $E_{666}/E_{573}$ |
|---|---|---|---|---|
| | | $E_{666}$ (cps × $10^{-6}$) | $E_{573}$ (cps × $10^{-6}$) | |
| no FA (control) | 0.302 | 1.07 | 1.22 | 0.88 |
| 0.015 | 0.326 | 1.26 | 1.14 | 1.11 |
| 0.05 | 0.359 | 1.38 | 0.63 | 2.19 |
| 0.15 | 0.338 | 1.43 | 0.40 | 3.58 |
| 0.50 | 0.367 | 1.45 | 0.38 | 3.82 |
| 1.00 | 0.357 | 1.46 | 0.36 | 4.06 |

Optimal preservation of energy transfer was obtained at 1% FA. Treatment with 2% FA for five hours provided equivalent protection.

Similar FA treatment conditions were required to stabilize phycobilisomes against dissociation in reduced ionic strength buffers. FA-treated phycobilisomes were diluted to approximately 0.75 ug/ml in 0.1 M KPi and left standing for 40 hours at room temperature. Fluorescence data for preparations treated with 1% FA for increasing intervals are summarized below:

| treatment time (hrsh) | Fluorescence (cps × $10^{-6}$ @ 0.75 ug/ml) | | Ratio $E_{666}/E_{573}$ |
|---|---|---|---|
| | $E_{666}$ | $E_{573}$ | |
| 0 | 0.45 | 6.25 | 0.07 |
| 2 | 1.88 | 1.02 | 1.84 |
| 5 | 2.06 | 1.00 | 2.06 |
| 18 | 2.31 | 0.91 | 2.54 |

To determine whether the stabilizing effect of FA was accompanied by formation of large, insoluble polymers of crosslinked phycobilisomes, FA-induced precipitation was estimated by centrifugation. Phycobilisomes were treated with FA concentrations up to 3.0%. Reactions were left standing at room temperature for 2–18 hours. Recovery of soluble, modified phycobilisomes was estimated by comparing 545 nm absorbance of thoroughly mixed preparations with supernatants obtained after two-minute centrifugation at 8000×g. Relative percent precipitation was determined by subtracting percent recovery of FA-treated preparations from untreated controls. Only prolonged treatments with high FA concentrations yielded significant precipitation.

| [FA] (%) | % recovery at treatment time = | | | relative % precipitation at time = | | |
|---|---|---|---|---|---|---|
| | 2 hours | 5 hours | 16 hours | 2 hours | 5 hours | 16 hours |
| 0 FA control | 95.7 | 96.0 | 95.4 | 0 | 0 | 0 |
| 0.5% | 93.5 | — | 97.0 | 2.2 | — | 0 |
| 1.0% | 93.7 | 96.6 | 94.6 | 2.0 | 0 | 0.8 |
| 2.0% | — | 92.4 | — | — | 3.6 | — |
| 3.0% | 92.0 | 78.6 | 40.1 | 3.7 | 17.4 | 55.3 |

No precipitation was observed in FA-modified phycobilisomes (2% FA×5 hours) left standing at room temperature for 18 weeks. In addition, no differences in recovery, conjugation efficiency or immunoassay performance were apparent using FA-treated phycobilisomes prepared with and without mixing. These results indicate that FA-treated phycobilisome preparations behaved as homogeneous solutions for purposes of protein modification, purification, immunoassay and prolonged storage.

FA-stabilized phycobilisomes were routinely stored at room temperature. Reference samples were refrigerated (2–8° C.) for stability comparisons. FA-stabilized phycobilisomes were characterized by absorption and fluorescence measurements using a Shimadzu Model UV-160 recording spectrophotometer and a SPEX FLUOROMAX fluorometer, respectively.

STABILIZATION EXAMPLE 3

Preparation of a Stable, Modified Phycobilisome Reagent Using Glutaraldehyde

Phycobilisomes were adjusted to a concentration of 2–10 mg/ml, preferably about 8.0 mg/ml, with 0.75 M KPi (pH 7.3) containing 0.05% sodium azide. GA (glutaraldehyde) (0.2–1.0% in 0.75 M KPi) was added dropwise with vortexing in a 10–50% volume over two minutes or, alternatively, in 3–6 incremental additions over elapsed periods up to three hours. Following addition of GA, the reaction mixture was left standing at room temperature for 1–18 hours. In a preferred stabilization protocol designed to precede conjugation by modified one-step GA methods, a reaction mixture comprising 7.27 mg/ml phycobilisomes plus 0.023% GA was incubated at room temperature for 3 hours before addition of a ligand (e.g., antigen) or receptor (e.g., antibody) containing primary amines. Alternatively, the GA stabilization reaction was terminated by addition of excess primary amines (e.g., 100 mM lysine, arginine, glycine, cysteine or glutamic acid). In a preferred protocol for GA stabilization prior to conjugation or immobilization through groups other than free aldehydes, phycobilisomes (7.27 mg/ml) were first stabilized for 1–2 hours with 0.023% GA followed by a 1–4 hour incubation with an additional 5–10 volumes of 0.05–0.15% GA. The reaction was terminated by addition of 100 mM lysine, glycine, cysteine, glutamic acid or an alternative primary amine-containing quench agent. GA-stabilized phycobilisomes were characterized by absorption and fluorescence measurements in accordance with methods used for unmodified phycobilisomes and FA-stabilized phycobilisomes.

Stabilized phycobilisomes from *P. cruentum* reproducibly met the following specifications:

| | |
|---|---|
| Absorptivity: | >4 $AU_{545}$/mg (mean about 5.0) |
| Fluorescence signal (666 nm): | >$10^4$ cps at 1 ng/ml with excitation at 545 nm |
| Fluorescence ratio: | 666/573 nm emission ratio > 3.0 with excitation at 545 nm |

The stabilizing effect of GA was titrated as follows. GA (0.03–3.0% in 0.75 M KPi) was added dropwise with mixing to phycobilisomes in 0.75 M KPi to yield reaction mixtures comprising 10 mg/ml phycobilisomes and GA at concentrations ranging from 0.003% to 0.3%. After 12 hours at room temperature, reactions were quenched with 100 mM glycine and stored at room temperature for two weeks prior to evaluation.

Stability to dilution was determined by incubating resultant preparations at 10 ug/ml for varying periods of time in 0.75 M KPi (pH 7.2). Concentrated phycobilisome stocks were diluted to 10 ug/ml at time zero. Emission spectra of diluted preparations were recorded at varying time intervals with 545 nm excitation. Fluorescence data are expressed as $E_{666}/E_{573}$ ratios. Time-zero ratios (30 seconds post-dilution) averaged 2.10 for untreated controls compared to 3.21 for 0.03% GA-treated phycobilisomes, indicating significant dilution-dependent dissociation of controls within 30 seconds.

| Treatment | Empirical result | Absorption: major peaks | $AU_{545}$ (10 ug/ml) | Post-dilution $E_{666}/E_{573}$ ratio | | |
|---|---|---|---|---|---|---|
| | | | | t = 1 hr | t = 18 hr | change |
| 0 GA control | homogeneous purple liquid | 545 > 565 | 0.052 | 1.04 | 0.70 | −33% |
| 0.003% GA | no apparent change | 545 > 565 | 0.049 | 1.31 | 0.98 | −25% |
| 0.01% GA | no apparent change | 545 > 350 | 0.051 | 2.05 | 1.72 | −16% |
| 0.03% GA | slightly hazy, trace settling | 545 > 565 > 350 | 0.055 | 3.04 | 3.01 | −1% |
| 0.10% GA | cloudy with aggregation | 545 > 350 | 0.051 | 3.41 | 3.23 | −5% |
| 0.30% GA | precipitation discoloration | 550 > 350 | 0.003 | ND | ND | ND |

Stabilization to reduced ionic strength by sub-precipitating concentrations of GA was assessed by monitoring fluorescence spectra of control vs. 0.03% GA-treated phycobilisomes following dilution in varying mixtures of deionized water and 0.75 M KPi. The stabilizing effect of 0.03% GA treatment was dramatically apparent within one hour of dilution:

| [KPi] (mM) | phycobilisome emission ($E_{666} \times 10^{-7}$ cps) following excitation at 545 nm | |
|---|---|---|
| | Untreated | GA-treated |
| 750 | 1.68 | 1.69 |
| 250 | 1.47 | 1.67 |
| 100 | 1.11 | 1.68 |
| 30 | 0.65 (shoulder) | 1.66 |
| 10 | 0.50 (no peak) | 1.61 |
| 0.75 ($H_2O$ diluent) | 0.46 (no peak) | 1.56 |

Details of the quench, reduction and purification steps of the GA (and FA) stabilization process were varied for different applications. Properties of aldehyde-treated phycobilisomes could be varied by quenching reactions with different amino acids (e.g., glycine, D-arginine, L-lysine). In addition, new chemical groups could be conveniently introduced by selecting suitable quench agents (e.g., L-cysteine for introduction of thiol groups, glucosamine for introduction of sugar groups). For example, phycobilisomes were treated with 0.023% GA, quenched with 10 mM L-cysteine and either stored for subsequent use or reduced, purified and conjugated as follows. Cysteine-quenched, GA-treated phycobilisomes were reduced with 30 mM dithioerythritol and purified over SEPHAROSE™ (beaded agarose) CL-6B equilibrated with 100 mM KPi containing 100 mM NaCl (pH 7.4). Pyridyl-derivatized streptavidin was prepared by established methods using SPDP in 100 MM sodium phosphate (pH 7.4) at an SPDP/streptavidin molar ratio of 10. The product was purified by dialysis in the same buffer and reacted with thiolated phycobilisomes at streptavidin/phycobilisome molar ratios ranging from 2 to 10. The thiolated phycobilisomes were added to the conjugation reaction immediately following reduction. Streptavidin-phycobilisome conjugates were purified over SEPHAROSE CL-6B. Biotin-specific binding was demonstrated using biotinylated BSA immobilized on paramagnetic particles as the capture reagent.

STABILIZATION EXAMPLE 4

Storage of Phycobilisomes and Modified Phycobilisomes in Dehydrated Form

Dry-reagent formats are preferred for many diagnostic tests and kits as a means of eliminating reagent addition steps, improving reproducibility and increasing shelf-life. Lyophilization (freeze-drying) is a common method of drying reagents for long-term storage. Literature suggests that phycobilisomes are unstable to freezing. (See, e.g., Gantt and Lipschultz (1972), "Phycobilisomes of *Porphyridium Cruentum*", *J. Cell Biol.*, 54:313–324; Canaani et al. (1980), "Reassembly of Phycobilisomes from Allophycocyanin and a Phycocyanin-Phycoerythrin Complex", *FEBS Letters*, 115 (2):225–229). Freeze-drying of phycobilisomes and conjugates was undertaken to establish feasibility of dry-reagent phycobilisome product formats.

Phycobilisomes were isolated from *P. cruentum* in 0.75 M KPi at 8.8–9.5 mg/ml. Three to twenty microliter aliquots (45–190 µg) were flash-frozen and vacuum evaporated in microtiter wells. The dried phycobilisomes were stored 0–4 weeks at room temperature, resuspended, diluted, and transferred to 3 ml cuvettes for absorbance and fluorescence measurements. Phycobilisomes stored 1S in buffered solution (8.8–9.8 mg/ml in 0.75 M KPi containing 0.05% sodium azide) were used as reference.

Absorbance was not affected, while fluorescence was affected slightly. Unmodified phycobilisomes survived freeze-drying and 4-week storage with no change in absorbance. There was a 15–20% decrease in both fluorescence intensity and the 666/573 nm emission ratio with freeze-drying and 4-week storage compared to untreated control. The only significant decrease in fluorescence of freeze-dried preps occurred from time 0 to week 1. No significant changes were noted on storage from week 1 through week 4.

Covalently stabilized phycobilisomes (phycobilisome-antibody conjugates) suffered substantial degradation immediately following freeze-drying in 100 mM M KPi containing 150 mM sodium chloride and 0.05% sodium azide. Fluorescence emission at 666 nm decreased by about 60%, 666/573 emission ratios decreased five-fold, and absorption spectra were perturbed. Addition of 1 M sucrose prior to lyophilization alleviated all signs of degradation. Conjugate freeze-dried in sucrose-supplemented KPi over 4 weeks showed no significant change in fluorescence or absorbance properties compared to liquid controls or time-zero freeze dried conjugates.

Derivatization of Phycobilisomes

Phycobilisomes according to this invention may be modified by covalent attachment of desired chemical moieties. For use in specific binding assays, phycobilisomes can be conjugated to ligands, receptors, and/or signal-generating molecules by one-step, two-step, or multi-step methods. One-step glutaraldehyde methods proved effective and convenient for sequential stabilization and conjugation of phycobilisomes without intervening purification steps. For achieving conjugation of phycobilisomes to other molecular species, any conjugation method known in the art may be used. Direct attachment may be used or secondary structures such as spacer arms, bridging groups, or carrier molecules may be interposed.

Specific chemical groups can be added to phycobilisomes by quenching the stabilization reactions with suitable substances, including but not limited to cysteine, lysine, glutamic acid, glucosamine, etc. Such chemical groups can be useful for the further coupling of distinct molecular species, such as receptors, ligands, or signal-generating molecules to phycobilisomes. Other examples of desirable molecular species include lipids, polysaccharides, or supramolecular complexes such as multisubunit enzymes or even viruses. Added functional groups can also be used to dimerize or polymerize the phycobilisomes for use as stabilized, isolatable complexes. In a particularly preferred embodiment, two or more different types of phycobilisomes can be conjugated to one another to produce a heteroconjugate capable of energy transfer from a donor phycobilisome to an acceptor phycobilisome.

Attached molecular species may be, but need not be, conjugated to phycobilisomes through added chemical groups. Alternatively, they can be directly attached during the stabilization reaction, such as with formaldehyde (FA) or glutaraldehyde (GA). They can also be attached via different spacer arms to alter the spatial or stereochemical relationship between the molecular species and the phycobilisome. Carrier molecules, such as bovine serum albumin or even virus particles, may be attached to phycobilisomes and function as a plurality of added chemical groups for attaching desired chemical moieties to the phycobilisome. Ligands include but are not limited to agonists, antagonists, biotin (or derivatives, such as amido-biotin, imino-biotin, and diamino-biotin), haptens, antigens, carbohydrates, drugs, hormones, transmitters, cofactors, vitamins, toxins, oligonucleotides, nucleic acids, aptamers, and conjugates formed by attaching any of these molecules to a second molecule. Receptors include but are not limited to antibodies, antibody fragments, antibody mimetics, molecular mimics and molecular imprints, molecular recognition units, adhesion molecules, soluble receptors, avidin, streptavidin, lectins, selecting, oligonucleotides, nucleic acids, membrane receptors, cellular receptors, and drug receptors. Signal-generating molecules include, but are not limited to, phycobiliproteins, dye molecules, colloids, fluorophores and other photoactive molecules, enzymes, ribozymes, molecular mimics, luminescent compounds, oxidizing and reducing compounds and other electroactive molecules, photosystem molecules and reaction centers not attached to phycobilisomes in nature such as artificial reaction centers and organizational and coupling molecules used to capture energy in artificial photosynthesis, and even other phycobilisomes.

DERIVATIZATION EXAMPLE 1

Specific Binding Assay Using Noncovalent Phycobilisome-antibody

Since unmodified phycobilisomes rapidly dissociate under conditions typically used for preparation and use of specific binding reagents, noncovalent phycobilisome conjugation required careful attention to phycobilisome concentration and reaction conditions at each step of the process. Murine monoclonal anti-phycoerythrin antibody of IgG2b subtype (Sigma Chemical Company) was added dropwise with vortexing to P. cruentum phycobilisomes (5.6 mg/ml) in 0.6 M KPi (pH 7.2) containing 2.5 mg/ml BSA to yield molar ratios ranging from 0.5–20 IgG2b/phycobilisome. The reaction was allowed to proceed for 30 minutes at room temperature. Immunologic conjugate formation was demonstrated by specific capture of IgG2b phycobilisome complexes using goat anti-mouse IgG2b antibody immobilized on paramagnetic particles. Fifty microliters of BIOMAG™ (paramagnetic particles)-goat-antimouse (GAM) IgG2b (30 mg/ml washed in 0.75 M KPi containing 1% BSA) was added to 40 ul of conjugate mixture containing 200 ug phycobilisomes. After addition of capture reagent, the assay mixture contained phycobilisomes at 2.2 mg/ml with or without bound IgG2b in 0.66 M KPi containing 6.7 mg/ml BSA. This mixture was incubated for 30 minutes at room temperature and separated on a magnetic base (Corning). Absorbance at 545 nm was measured using assay supernatants diluted 40-fold in 0.75 M KPi. A dose-dependent decrease in absorbance with increasing IgG2b was observed, indicating specific binding of the phycobilisome-IgG2b complex by BIOMAG-GAMIgG2b. Maximal specific binding (26%) occurred at 1–3 ug/test IgG2b, above which binding decreased due to insufficient solid phase capacity.

DERIVATIZATION EXAMPLE 2

Preparation of Phycobilisome-antibody Conjugate

All steps were performed at room temperature (20–23° C.). Phycobilisomes, isolated from P. cruentum were normalized to a concentration of 8 mg/ml in 0.75 KPi (pH 7.35) containing sodium azide (2 mM). GA (0.25%) was added dropwise with vortexing over 2 minutes in a 10% volume to yield a reaction mixture containing phycobilisomes at 7.27 mg/ml and GA at 0.023%. The reaction mixture was left standing for 2 hours. Affinity-purified, Fc-specific goat anti-mouse IgG (GAM; OEM Concepts; 2 mg/ml in 10 mM phosphate-buffered isotonic saline containing 0.1% sodium azide) was added dropwise with vortexing to yield a GAM/phycobilisome molar ratio of 12:1 (128 ug GAM per mg phycobilisomes). After a 4-hour incubation, the reaction was terminated by addition of a 10% volume of 1.1 M L-lysine. The quenched reaction was mixed by rotation for one hour. A 5% volume of freshly prepared sodium borohydride (Aldrich; 5 mg/ml in 0.1 mM NaOH) was spiked into the reaction mixture with vortexing, followed 5 minutes later by a 10% volume of the same solution. The borohydride-reduced reaction mixture was stored at 2–8° C. until purification by ultracentrifugation or, preferably, gel chromatography using SEPHACRYL™ (cross-linked co-polymer of allyl dextran and N,N'-methylenebisacrylamide) S300 or Sepharose CL-6B (Pharmacia) equilibrated in 100 mM KPi (pH 7.35) containing 150 mM NaCl and 0.05% $NaN_3$.

The conjugates were assessed on the basis of: % recovery (yield of soluble phycobilisome conjugate as a percentage of phycobilisome starting material, accounting for procedural losses); absorptivity (AU/mg); fluorescence (concentration-normalized emission intensity; peak ratios); and specific binding in a competitive fluoroimmunoassay using BIOMAG-MIgG as solid phase capture reagent.

Recovery of soluble material estimated for conjugates purified by ultracentrifugation ranged from 72–100%, averaging about 90%. Twelve conjugates prepared from a single lot of phycobilisomes yielded $E_{666}/E_{573}$ ratios of 2.92–3.55 (mean=3.16). Normalized fluorescence intensity ($E_{666}$ at fixed input) averaged $4.15\times10^6$ cps at a conjugate concentration of 1 ug/ml.

Up to 60% specific binding of conjugates to BIOMAG-MIgG was demonstrated with the solid phase reagent in pseudo-excess (complete saturation was not attempted). Representative binding data are presented below. Fifty microliters of phycobilisome-GAM conjugate (80 ug/ml) was added to test tubes containing 50 ul of buffer with or without MIgG plus 100 μl BIOMAG-MIgG (1 mg/test). Assay tubes were vortexed and incubated for 60 minutes at room temperature. Fluorescence was determined in a volume of 3 ml using 160 ul of assay supernatant withdrawn after magnetic separation.

| MIgG (mass/test) | Supernatant $E_{666}$ (cps × $10^{-5}$) | % bound | MIgG inhibition (cps × $10^{-5}$) |
|---|---|---|---|
| 0 | 22.44 | 42.1 | — |
| 1 ng | 27.91 | 28.0 | 5.47 |
| 10 ug | 38.77 | 0.0 | 16.33 |

GA was also used to conjugate GAM antibody to FA-stabilized phycobilisomes. Phycobilisomes were treated with 2% FA for four hours, quenched with 1 M L-lysine and chromatographed over Sepharose CL-6B. Stabilized phycobilisomes appearing in the void volume were treated with GA and reacted overnight with antibody at a 12:1 molar ratio. Lysine quench, borohydride reduction and purification were performed as per GA conjugation methods (supra). Resultant conjugates exhibited 666/573 ratios over 3.0 and 60% specific binding to BIOMAG-MIgG. No significant decrease in fluorescence intensity ($E_{666}$) or immunoreactivity (% binding) was detected with overnight room temperature storage at a working concentration in 10 mM KPi-based assay buffer or with storage for one week in 100 mM KPi-based assay buffer.

Site- or Regio-specific Derivatization

Attachment of a molecular species to a phycobilisome may be site-specific or regio-specific, for example, by derivatizing a particular portion of a phycobilisome to orient the light collection properties of this invention. Site-specific or regio-specific attachment means preparation of a conjugate comprising a phycobilisome and a second structure (e.g., a second molecular species, a new chemical group or plurality of new chemical groups, or a solid support), wherein the second structure is attached to the phycobilisome at chemically, functionally or topologically defined site(s). Site-specifc attachment involves attachment to a particular chemical moiety, such as a reactive group or a site that specifically binds an affinity reactant, while for regio-specific attachment, the focus is on toplogical position of the attached species rather than on the particular chemical site. However, the art recognizes some overlap between these terms.

Site-specific attachment may be covalent or non-covalent. Preferred attachment site(s) vary depending on the application and the composition of the phycobilisomes to be used. For a single rod, preferred sites include the cap polypeptide (i.e., "cap protein"), sensitizing biliproteins making up the outermost discs, the terminal acceptor, and the rod or rod-core linker polypeptide(s). For a rod-core subassembly, preferred sites include cap proteins, sensitizing biliproteins of the rod(s) and the terminal acceptor and linker polypeptide(s) of the core. For phycobilisomes further comprising an anchor polypeptide and/or reaction center and/or photosystem, specific polypeptides or proteins or peptide sequences or amino acid residues can serve as targets for site-directed attachment. In each case, wild-type proteins and peptides can be replaced by mutant, recombinant or chemically modified sequences or residues to introduce distinct reactive groups in topologically or functionally preferred sites. For example, one or more phycobilisome proteins can be glycosylated (e.g., by periodate or hydrazide chemistry) and the saccharide residues specifically bound by lectin-conjugates of molecular species, such as signal-generating molecules.

Site-specific or regio-specific attachment of a molecular species to a phycobilisome may be achieved inter alia by means of monovalent or polyvalent receptors, such as antibodies or other peptides, which are specific for one of the component proteins of the phycobilisome. A polyvalent receptor contains two or more binding sites for its ligands. The polyvalent receptors utilized in the present invention may be polyspecific, i.e., they may contain binding sites for two or more distinct ligands. Thus, the polyspecific receptors can be used to link a phycobilisome to another species of molecule. Alternatively, site-specific attachment to phycobilisomes by non-coralent means can be achieved using peptides or other heteropolymers selected by combinatorial methods (see, e.g., Fodor, et al., 1991, *Science*, 251:767–772; Kauffman, S. (1994), "Random chemistry," *Ber. Bunsenges. Phys. Chem.*, 98:1142–1147; Kenan, D. J., et al. (1994), "Exploring molecular diversity with combinatorial shape libraries," *Trends in Biological Sciences (TIBS)*, 19:57–64; Ostresh, J. M. et al. (1994) "Libraries from libraries: Chemical transformation of combinatorial libraries to extend the range and repertoire of chemical diversity," *Proc. Natl. Acad. Sci. USA*, 91:11138–11142; Hart, S., 1993, "Test-tube survival of the molecularly fit," *BioScience*, 43:738–741). Phycobilisomes can also be covalently attached to receptors or ligands by numerous methods well-known in the art of protein conjugation (cf. Tijssen[1], Wong[2] and Pierce[3] and references therein, included herein by reference), and the attachment may include the use of intervening spacer arms, bridging groups, carrier molecules, and the like.

[1] Tijssen, P. (1985). *Practice and Theory of Enzyme Immunoasaays*. R. H. Burdon and P. H. van Knippenberg (Eds.) Laboratory Techniques in Biochemistry and Molecular Biology, Volume 15, Elsevier, New York.
[2] Wong, S. S. (1991). *Chemistry of Protein Conjugation and Crosslinking*, CRC Press, Boca Raton.
[3] Pierce Catalog & Handbook (1994) Cross-linking/Protein Modification, pp. 155–200.

Site-specific attachment may also be achieved through monospecific and monovalent ligands or receptors. For example, an antibody specific for a particular site on the phycobilisome can be reduced to yield two half-antibody molecules containing free sulfhydryl groups. The reduced product can then be specifically bound to the phycobilisome to provide a unique conjugation site for a sulfhydryl-reactive conjugation reagent. Alternatively, the half-antibody molecules can be conjugated either through the free sulfhydryl groups or amines or carboxyls or the carbohydrate chains of the $C_H2$ domain to a second molecule, e.g., a different ligand or receptor or signal-generating molecule. The conjugate can then be specifically bound to the targeted site on the phycobilisome. The same technique can be used to target Fab fragments or conjugated Fab fragments to phycobilisomes by first preparing enzymatic digests of an antibody against a phycobilisome constituent. $F(ab')_2$ fragments prepared in this way can be reduced to yield monovalent Fab' fragments with free sulfhydryl groups. Because these monospecific, monovalent fragments are significantly smaller than intact antibody molecules, they are preferred for certain applications that require functional coupling between phycobilisomes and attached signal-generating molecules. For example, anti-allophycocyanin (anti-APC) Fab' fragment can be conjugated to a ligand such as a hapten (e.g., a drug, hormone, pesticide or other analyte) or a DNA probe (e.g., for detection of a target nucleic acid sequence) so that the conjugated phycobilisome can serve as a label for specific binding reactions localized to a particular region of the phycobilisome. In this mode of operation, the phycobilisome conjugate functions as a directional light-harvesting antenna coupled to a specific binding reaction.

Using an antibody directed against a phycobilisome constituent for regio-specific recognition, attachment can also be directed to the carbohydrate groups of the $C_H2$ domain of the Fc region, e.g., by periodate oxidation of the polysaccharide sugar residues to generate aldehydes followed by modification or crosslinking with a hydrazide reagent (e.g., Wong (1991), Pierce (1994)).

Alternatively, noncovalent attachment of a ligand, receptor or signal-generating molecule to carbohydrates in the Fc region of an anti-phycobiliprotein or anti-linker polypeptide antibody can be achieved using an affinity reagent, e.g., a lectin or selectin with suitable sugar specificity.

Additional techniques for site-directed attachment include, without limitation, genetic methods, preparative modifications, interfacial methods, reconstitution of phycobilisomes with genetically or chemically modified or immobilized constituents and self-assembly of conjugates comprising selected molecules non-covalently attached to phycobilisomes. Genetic methods include, for example, use of site-directed mutagenesis, recombinant techniques and fusion proteins to incorporate a unique attachment site (e.g., a poly-his region or surface cysteine residue or amino acid analog) in a particular linker polypeptide or protein, and use of applied molecular evolution to screen and select linker polypeptide and phycobiliprotein variants for desired recognition properties or attachment sites.

Regio-specific modification or conjugation can also be directed to functional groups on or near the biliprotein chromophores or their apoprotein attachment sites. The tetrapyrrole groups of phycocyanobilin, phycobiliviolin, phycoerythrobilin and phycourobilin and the thioether linkages between the chromophores and the apoproteins comprise functional groups not represented on the phycobilisome surface. These groups provide targets for genetic and chemical modification, and such modification can and typically does alter the spectral properties of the modified products relative to unmodified phycobilisomes. For certain applications (e.g., use of phycobilisomes as sensitive labels for homogeneous specific binding assays), it is preferable to regio-specifically modify phycobilisomes without perturbing absorption and fluorescence properties. For other applications (e.g., use of two or more phycobilisome labels in multicolor flow cytometry or multiplexed sensors), it is preferable to co-select among multifactoral combinations of modification reagents (e.g., number and type of reactive groups, length of spacer arm(s)) and reaction conditions (e.g., reagent concentrations, reaction time, temperature, pH, solvent and buffer conditions) and phycobilisome preparations (e.g., source, isolation procedure, stabilization protocol) those modified products that exhibit the most desirable spectral properties. In a particularly preferred embodiment, phycobilisomes modified near biliprotein chromophores are reconstituted from isolated linker polypeptides and phycobiliproteins which have been site-specifically modified by chemical, affinity-based or genetic methods disclosed elsewhere in this specification.

Regio-specific modification of phycobilisomes according to this invention includes stabilization of phycobilisomes in situ (e.g., Clement Metral et al. (1971)) so that peripheral rods are exposed to the solution phase, but thylakoid membrane-embedded constituents are inaccessible to water-soluble conjugation reagents. The peripheral rod side of the phycobilisome can then be selectively modified without altering constituents embedded in the membrane. Phycobilisome modification conditions can then be adapted to either encourage or discourage reagent access to sterically or kinetically hindered sites near the core-membrane interface. Alternatively, functional groups of the peripheral rods (e.g., amine or carboxyl groups) can be selectively blocked. Stabilized, partially blocked phycobilisomes can then be isolated from thylakoid membranes, leaving membrane-protected sites of the core side available for conjugation. A similar method can be developed using affinity reagents with bulky substituents to sterically occlude targeted regions of the phycobilisome (e.g., the terminal acceptor or APC core) followed by rapid modification of the most accessible sites, e.g., using a photoactivatable crosslinker with pulsed illumination, a photo-affinity reagent, an immunoaffinity conjugate, or the like. Alternatively, regio-specific binding to a phycobilisome may be accomplished using a reagent that specifically recognizes sites distributed over the entire surface by covalently blocking a portion of the specific sites on the phycobilisome and then non-covalently binding the reagent to the unblocked sites.

Interfacial methods rely on the structural orientation of phycobilisomes or the relative solubility of phycobilisomes and a second molecular species exposed to a two-phase system, e.g., a polar-nonpolar solvent mixture or solid-liquid interface. Aqueous-nonpolar two-phase solvent systems can be selected to partition the hydrophilic, biliprotein-rich side of the phycobilisome to the aqueous phase while favoring association of the hydrophobic anchor polypeptide with the nonpolar phase. Alternatively, a particular region of the phycobilisome can be rendered especially hydrophobic using an affinity reagent conjugated to a hydrophobic or lipophilic substituent (e.g., a lipid or colloid or polymer). Similar effects may be achieved by regio-specific derivatization of phycobilisomes with either hydrophilic moieties or lipophilic moieties using derivatization techniques described above. Phycobilisomes can also be oriented electrophoretically (e.g., Gagliano et al. (1985)) followed by regional modification through transient exposure of one side of the gel to a selected protein modification reagent. Similar methods can be developed using affinity supports to orient the phycobilisome on a matrix and to preferentially occlude particular region(s) of the phycobilisome, e.g., the anchor polypeptide or terminal acceptor. Solid-liquid phase systems provide preferential access of conjugation reagents to the solution phase side of the phycobilisome and impaired access to the solid phase side. Phycobilisomes can be oriented on a solid phase by self-assembly using hydrophobic or amphipathic membranes, films, polymers or coatings. Alternatively, the desired orientation can be achieved using affinity-based methods, e.g., by specific binding to an immobilized anti-APC, anti-linker polypeptide, or anti-anchor polypeptide antibody.

Phycobilisomes may also be immobilized to a manufactured solid support, such as a microtiter dish, microparticle, polymeric bead, polymer matrix, polymer, synthetic membrane, liposome, glass, etc. Such immobilization does not include the attachment of phycobilisomes to the thylakoid membrane as occurs physiologically, via specific receptors in the thylakoid membrane. The phycobilisomes may first be isolated from algal cells and then attached to the solid support, or they may be modified, conjugated, or stabilized, prior to attachment. The attachment may be covalent or noncovalent, specific or nonspecific. The method of attachment may be optimized to achieve a preferred orientation of the phycobilisomes relative to the solid surface. In one embodiment, phycobilisomes derivatized with lipophilic moieties, such as fatty acids or fatty acid analogs, may be immobilized by hydrophobic partitioning of lipophilic moieties into a lipid bilayer membrane. Optionally, the lipid bilayer membrane may itself be immobilized on a solid support. Alternatively, a single type of constituent phycobilisome protein, either linker polypeptide, anchor protein or phycobiliprotein, may be used as the attaching moiety to a solid support. For some applications, it may be desirable that the phycobilisomes be attached in an ordered array, such as in a grid or other pattern.

Self-Assembly of Phycobilisomes

Phycobilisomes, isolated as described herein, are capable of self-assembly after gentle dissociation. After gentle dissociation in low ionic strength buffers, native phycobilisomes will spontaneously self-assemble when the buffer concentration is increased, e.g., to 0.75 M phosphate. Reassociation is driven by one or more specific linker polypeptides that recognize the constituent phycobiliproteins and arrange them into a very efficient energy transduction system in a non-covalent manner. Self-assembly is a powerful tool that enables production of novel and useful compositions, e.g., stabilized and conjugated and immobilized hybrid or chimeric phycobilisomes, and methods, e.g., attachment and functional coupling of phycobilisomes and chimeric phycobilisomes to transducers by self-assembly (which may be followed by stabilization and/or conjugation).

There is a broad literature on the dissociation and reassociation of phycobilisomes (e.g., Canaani et al. (1980) *FEBS Letters,* 115:225–229; Lipschultz and Gantt (1981) *Biochemistry,* 20:3371–3376; Cananni and Gantt (1982) *Proc. Nat. Acad. Sci. USA,* 79:5277–5281; Glick and Zilinskas (1982) *Plant Physiol.,* 69:991–997; Zilinskas and Howell (1983) *Plant Physiol.,* 71:379–387; Isono and Katoh (1983) *Plant Cell. Physiol.* 24:357; Cananni and Gantt (1983) *Biochim. Biophys. Acta,* 723:340). This self-assembly of the phycobilisome can be used to create chimeras using components from different phycobilisomes (from different organisms). Any such chimera (or hybrid) may have properties (e.g., absorbance or fluorescence emission, quantum yield) which differ from the parent phycobilsomes in a manner useful for detection and signal transduction. In addition, the self-assembly can be used in assays based on proper assembly of the complex (e.g., phycoerythrin/phycocyanin rod association via a specific binding reaction to the allophycocyanin core yielding emission at 666 nm).

An example of how self-assembly works is described here. Phycobilisomes may be dissociated at defined concentrations of phosphate buffer such that peripheral phycobiliproteins are dissociated first (Nies and Wehrmeyer (1981) *Arch. Microbiol.,* 129:374–379). This approach has been described previously for a number of organisms (Gantt et al.(1979) *Plant Physiol.,* 63:615–620; Cananni et al. (1980) *FEBS Letters,* 115:225–229); optimization for phycobilisomes from other organisms can be accomplished by placing them in a phosphate concentration that differentially destabilizes the phycobilisomes and then dialyzing. After about 3 hours the material is centrifuged to pellet the phycobilisomes, while dissociated phycobiliproteins remain in the supernatant. This can be done in a sequential manner to release the phycoerythrins, phycocyanins and allophycocyanin in a stepwise fashion. These components can then be reassociated by putting the fractions together at a phosphate concentration (e.g., 0.75 M) that favors reassociation. For in vitro association, fractions may be mixed at 0.75 M potassium phosphate (pH 7.0) containing 2 M sucrose and incubated for 3 h. Samples of this reassociation mixture can then be put over a discontinuous sucrose gradient and centrifuged to equilibrium. Intact, functionally active phycobilisomes may be isolated in the 1–2 M sucrose fraction. Hybrid phycobilisomes can be prepared by this method, so long as the linker polypeptides are compatible (e.g., by mixing the allophycocyanin fraction from Fremyella with the phycocyanin/phycoerythrin fraction from Nostoc, Canaani and Gantt (1982) *Proc. Nat. Acad. Sci. USA,* 79:5277–5281).

Where the intention is to specifically label the phycobilisome at the core (allophycocyanin) or terminal emitter region, the allophycocyanin fraction can be isolated and biotinylated using NHS-biotin (PIERCE CHEMICAL COMPANY). Once biotinylated, the allophycocyanin fraction may be added back to the phycocyanin/phycoerythrin fraction and allowed to reassociate. The reassociated phycobilisome now has biotin on the terminal emitter such that streptavidin chemistry can be used to specifically label the terminal emitter, to attach the phycobilisome through the terminal emitter for functional coupling, or to add additional reactive groups.

Phycobilisomes and hybrid structures can also be oriented in a site-directed manner on a solid support by reconstitution from partially dissociated phycobilisomes or isolated phycobiliproteins and linker polypeptides in the presence of an immobilized phycobilisome constituent, e.g., a linker polypeptide, anchor polypeptide or reaction center. The immobilized phycobilisome constituent can be directly attached to a solid support, or it can be specifically bound to an immobilized ligand or receptor or attached through a membrane or film or polymer or coating.

Self-assembly of phycobilisomes having exogenous hydrophobic molecules complexed to the anchor polypeptide can also be achieved. The biliprotein molecules of the phycobilisome are acidic and hydrophilic. The linker polypeptides, by contrast, are basic and very hydrophobic (Glazer, A. N. 1984, "Phycobilisomes: a macromolecular complex optimized for light energy transfer," *Biochim. Biophys. Acta,* 768:125–157; Glazer, AN., 1985a, "Light harvesting by phycobilisomes," *Annual Rev. Biophys. and Biophys. Chem.,* 14:47–77). There is therefore a tendency for added, water-insoluble molecules to associate with the exposed anchor polypeptide region by hydrophobic interactions. Methods can be developed to attach hydrophobic molecules, complexes or groups of molecules to the anchor polypeptide region by selecting the solvent system, molar ratio, assembly conditions and purification methods appropriate to the selected molecule. Alternatively, hydrophilic molecules or complexes can first be conjugated to a hydrophobic carrier and then attached by hydrophobic interactions to the anchor polypeptide region. Molecules or conjugates attached to specific phycobilisome regions in this manner can then be covalently attached by crosslinking methods well-known in the art. In a preferred embodiment, phycobilisomes or subassemblies are modified with hydrophobic, lipophilic or amphipathic substituents and incorporated or reconstituted in hydrophobic or amphipathic matrices by self-assembly, e.g., within a liposome, monolayer, film, membrane or membrane mimetic. Suitable hydrophobic and amphipathic matrices are well-known in the art (e.g., U.S. Pat. Nos. 3,966,580 (1976) and 4,490,216 (1984); Betageri, et al. (1993), *Liposome Drug Delivery Systems,* Technomic Publishing Company, Lancaster, Pa.; Gregoriadis, G. (Ed.) (1993), *Liposome Technology,* Volumes 1, 2 and 3, Boca Raton, Fla., CRC Press; Guo, et al. (1990), "Novel antifungal drug delivery: stable amphotericin B-cholesterol sulfate disks," *Int. J. Pharm.,* 75:45–54; Fendler, J. H. (1982) *Membrane Mimetic Chemistry,* Wiley-Interscience, N.Y; Janoff, et al. (1988), "Unusual lipid structures selectively reduce the toxicity of amphotericin B," *Proc. Natl. Acad. Sci.* USA, 85:6122–6126; Machy, et al. (1987), *Liposomes in Cell Biology and Pharmacology,* John Libbey Eurotext, London).

Phycobilisome preparations comprising reaction centers and photosynthetic constituents can also be prepared and modified to provide stabilized phycobilisomes, phycobilisome complexes or conjugates or immobilized reagents of the instant invention (Clement-Metral and Lefort-Tran (1971) *FEBS Letters,* 12:225–228; Gantt et al. (1988) *Meth. Enzymology,* 167:286–290). A phycobilisome-photosystem II complex has been isolated (Gantt et al. (1988) *Meth. Enzymology,* 167:286–290). The cells were rinsed in distilled water then suspended using a glass homogenizer in a buffer (0.5 M sucrose, 0.5 M potassium phosphate (pH 7.0), 0.3 M potassium citrate, 15 mM $MgCl_2$) at 4° C. The cells were broken in a French pressure cell. To this lysate, 0.12% (v/v) lauryldimethylamine oxide (LDAO) detergent was added to give a detergent to chlorophyll ratio of 3.5–4.1:1 (w/w). This mixture was incubated for 30 min in the dark with gentle stirring. The extracted lysate was centrifuged at 27,000×g for 30 min. The clarified lysate was placed on a discontinuous sucrose gradient and centrifuged at 130,000×g for 11 h. The phycobilisome-PSII complex was collected between the 1 M and 2 M sucrose layers. This was diluted to twice the volume with the original buffer and centrifuged at 27,000×g for 30 min. The supernatant contained the phycobilisome-PSII complex which can be used as is or can be concentrated by ultracentrifugation at 270,000×g for 3 h. This preparation method can be used for red algae and, with modification, for cyanobacteria.

Preparations comprising phycobilisomes bound to thylakoid membranes (e.g., Clement-Metral and Lefort-Tran (1971) *FEBS Letters,* 12:225–228; Katoh and Gantt (1979) *Biochim. Biophys. Acta,* 546:383–393; Laczkó and Kaiseva (1987) *Photochem. Photobiol.,* 46:421–425 can also be used to produce stabilized or conjugated or immobilized phycobilisomes or phycobilisome complexes of the instant invention. In one method (Clement-Metral and Lefort-Tran (1971) *FEBS Letters,* 12:225–228), whole algal cells were treated with 2% w/v glutaraldehyde for 15 min at 4° C. These cells were then washed twice in 0.02 M phosphate buffer (pH 6.9) by centrifugation. This procedure can be modified by methods of the instant invention to include quench and/or reduction steps prior to centrifugation to obviate excessive cell and membrane cross-linking. Quenching may be achieved by addition of excess amines (e.g., polylysine, lysine, glycylglycine, glutamine), and reduction may be achieved using borohydride, cyanoborohydride, dithiothreitol and the like. The washed cells are then disrupted by French pressure cell treatment and the lysate centrifuged 30 min at 12,000×g. The clarified supernatant is put on a 3–48% linear sucrose gradient and centrifuged for 5 h at 22,500 rpm on a Spinco SW25.1. A heavily pigmented layer in the middle of the gradient contains stabilized phycobilisomes attached to membrane fragments.

Use of Modified Phycobilisomes

Phycobilisomes as Detectable Labels

The phycobilisomes of the present invention are particularly well-suited for use in specific binding assays. These may be immunological assays, immunohistochemistry, cytometry, cell sorting, ligand- or receptor-binding assays, protein-protein binding assays, protein-nucleic acid binding assays, and even nucleic acid-nucleic acid binding assays (e.g., hybridization). The phycobilisomes are typically used to label one of the specific binding partners involved in the assay. For example, the phycobilisomes may be used to label a ligand or receptor that specifically binds to the analyte to be assayed. Alternatively, the phycobilisomes may be used to label a reagent molecule which is a ligand or receptor that competes with the analyte for specific binding to its specific binding partner. Labeling may be direct, where the phycobilisomes are attached to a first ligand or receptor that specifically binds to or competes with the analyte. Alternatively, labeling may be indirect, where the phycobilisomes are attached to a second ligand or receptor that specifically binds to a first ligand or receptor. The attachment of phycobilisomes to a specific binding partner may be covalent or noncovalent and may be accomplished using intervening chemical groups such as spacer arms, bridging groups, carrier molecules, molecular complexes, and the like. The phycobilisomes may also be part of a signal-generating system in which other fluorophores emit light upon transfer of directional energy to or from phycobilisomes. The phycobilisome may be stabilized prior to its attachment to the specific binding partner or may be directly conjugated thereto. Alternative means of preparation of phycobilisomes include freezing, freeze-drying, and other methods of dehydration. It is desirable that freezing of phycobilisomes be done in the presence of sucrose, in concentrations from 0.1 to 1 M. Other stabilizing agents such as sugars, salts, polymers, and cosolvents may be used. Particularly useful agents include trehalose, sorbitol, and dextran.

Soluble, stabilized phycobilisomes of the present invention have a number of uses that do not require conjugation to specific binding partners. For example, they can be used as sensitive tracers for dilution and perfusion studies and as molecular size markers for analytical techniques. In a preferred embodiment, they can be used to detect potentially hazardous spills. Phycobilisomes can be mixed with a potentially hazardous substance prior to its use to yield a final concentration of phycobilisomes of less than about ten parts per million. The phycobilisomes can then be detected in the event that the hazardous substance is accidentally spilled or removed from its proper location. The presence of the detectable phycobilisomes indicates that a spill has occurred. Alternatively, a first surface, substance or item can be treated with a coating or solution of phycobilisomes (and optionally allowed to dry), so that the appearance of detectable phycobilisomes on a second surface, substance or item indiates that a transfer of material has occurred, potentially including hazardous or otherwise undesireable contamination.

Specific binding assays according to the present invention may be qualitative or quantitative. Small molecules (involving a single binding site) or large molecules (involving more than one binding site) may be used as analytes. Analytes which may be measured or detected using specific binding assays according to the present invention include drugs, ligands, antigens, antibodies, carbohydrates, hormones, and the like. Detection means for determining the results of the binding assay may be by visual inspection, photometry, fluorometry, laser, or electrochemical means.

Any assay format known in the art may be utilized, including without limitation, homogeneous assays, heterogeneous assays, competitive assays, and sandwich assays. In homogeneous assays, specific binding between two binding partners (i.e., ligand and receptor) influences activity of a detectable label; no separation of bound and unbound reagents is required. In heterogeneous assays, separation of bound and free reagents is required to determine the amount of binding which has occurred. Quantification of such assays can be accomplished by either photometric, fluorometric or optoelectronic means. Alternatively, qualitative results can be obtained by visual inspection. Because native phycobilisomes spontaneously dissociate under routine conjugation and assay conditions, they must be stabilized prior to use in most conventional assay formats. However, in some instances it will be desirable to use the dissociation of phycobilisomes to amplify the signal generated. Thus, after using phycobilisomes in an assay and prior to detection, dissociation may be induced in order to take advantage of the individual fluorescent properties of the constituent phycobiliproteins.

Another means of using phycobilisomes to amplify a specific binding assay-signal is to use two or more labeled species specifically bound to one another, where at least one label is a phycobilisome. This approach is analogous to the well-known assay technique of using a labeled secondary antibody to amplify a primary immunological binding reaction. For phycobilisome-based signal amplification, it is preferred that both a primary and secondary specific binding reagent be labeled. For example, a secondary phycobilisome-labeled species (e.g., a phycobilisome-streptavidin conjugate) may be bound to a primary phycobilisome-labeled species (e.g., a biotinylated phycobilisome-antibody conjugate) via a secondary ligand-receptor pair (in this case, biotin-streptavidin). The use of secondary labeling is well-known in the art, as exemplified by such commonly used ligand-receptor pairs as avidin and biotin, fluorescein and anti-fluorescein, peroxidase and anti-peroxidase, digoxigenin and anti-digoxigenin, antibody and anti-antibody, or oligonucleotide probe and target. Thus, any ligand-receptor pair, such as biotin and avidin, can act as a bridge, linking primary and secondary labels. Phycobilisome-based amplification can be achieved in this manner using phycobilisomes as either primary label, secondary label, or both. Phycobilisomes are particularly advantageous as the primary label for amplification of this sort, because phycobilisomes can serve as particularly large scaffolds to hold a large number of secondary labels. It will be apparent to one skilled in the art that complexes of primary and secondary or even additional labels may be preformed prior to adding the label species to the assay. The primary and secondary or other labels may be phycobilisomes with different spectral properties.

In heterogeneous specific binding assays, a reaction mixture is formed by contacting a liquid medium with a labeled conjugate comprising a phycobilisome attached to a specific binding partner. A bound phase and a free phase of said labeled conjugate are formed. The relative proportion of labeled conjugate in the two phases is a function of the presence and amount of analyte in the liquid medium. The bound phase and free phase are then separated. The analyte in the liquid medium is determined by detecting or measuring phycobilisomes in the bound phase or in the free phase.

Particularly useful heterogeneous assays employ a solid phase, to which either the analyte or an analyte analog or a specific binding partner is attached. The solid phase facilitates the separation of bound labeled species from free labeled species in a heterogeneous specific binding assay. Popular solid phase reactions include Southern, Northern, and Western blotting assays. Any suitable solid phase can be used, chosen for its acceptability in a particular assay environment. These include synthetic membranes, polymers, microparticles, and glass.

A homogeneous specific binding assay method can also be readily performed. In a preferred method, a phycobilisome-labeled ligand or receptor is used in conjunction with a second fluorophore-labeled specific binding partner. Directional energy transfer within phycobilisomes enables their use as particularly efficient photon donors or acceptors in such fluorescence energy transfer assays, although such internal energy transfer is not absolutely required. For example, an anti-allophycocyanin (anti-APC) Fab' fragment labeled to high specific activity with a near infrared cyanine dye such as CY5.5 (Amersham Life Science, Arlington Heights, Ill.) can be used to attach and functionally couple the dye to a rhodophytic or cyanobacterial phycobilisome which has peripheral rods attached to a phycocyanin/allophycocyanin core. Excitation of the phycobilisome anywhere within its broad absorption spectrum then results in efficient energy transfer to the CY5.5 dye, as evidenced by an emission peak around 692 nm, representing an infrared shift of about 30 nm compared to the unmodified phycobilisome.

In a particularly preferred embodiment, an antibody or Fab fragment or other receptor or ligand specific for a phycobilisome constituent can first be specifically bound to a selected site on the phycobilisome and then covalently crosslinked in place using, e.g., FA or GA or other homobifunctional or heterobifunctional crosslinking agents well-known in the art (e.g., Tijssen (1985), Wong (1991) and references therein) which are available with or without variable length spacer arms (e.g., Pierce Catalog & Handbook (1994)). In another preferred mode of operation, an anti-APC or anti-anchor polypeptide Fab fragment can be labeled with both a signal-generating molecule (e.g., an acceptor fluorophor such as CY5.5) and a specific binding partner (e.g., a hapten or DNA probe). In this type of embodiment, specific binding of an anti-hapten antibody or nucleic acid target to the noncovalent, functionally coupled phycobilisome-conjugate complex can dissociate the complex, resulting in an analyte-specific signal (e.g., the spectral shift resulting from the uncoupling of energy transfer as the CY5.5-labeled Fab fragment dissociates from the phycobilisome). This type of reagent complex can be used for homogeneous specific binding assays, as specific binding directly influences the energy transfer activity of the phycobilisome-acceptor complex without the need for physical separation and wash steps.

Energy Transfer via Phycobilsomes

A number of earlier methods and compositions rely on high molecular weight complexes, polymers, particles and colloids to produce highly detectable labels. Urdea et al. (U.S. Pat. No. 5,124,246), for example, disclose linear or branched oligonucleotide multimers useful as amplifiers in biochemical assays. DNA dendrimers that provide a generic method for signal amplification are described in U.S. Pat. Nos., 5,175,270; 5,484,904; and 5,487,973. High molecular weight fluorescent proteins and dextrans are also known in the art, as are synthetic dye polymers (e.g., U.S. Pat. No. 5,019,521). High intensity fluorescent microspheres comprising multiple energy transferring dyes with suitable spectral overlap to yield single a emission peak at a selected wavelength are described in U.S. Pat. No. 5,326,692.

The phycobilisomes, stabilized phycobilisomes, modified phycobilisomes and phycobilisome complexes disclosed herein provide an important, distinct and useful property that is absent in above-cited art. Phycobilisomes function in nature as antenna structures that efficiently harvest light. The light-harvesting properties of phycobilisomes depend on an intrinsic structural and functional "sidedness," meaning that photons are collected from one "side" (i.e., peripheral rod(s)) and re-emitted from a second "side" (i.e., the terminal acceptor). Directional energy transfer can be demonstrated in phycobilisomes comprising a single rod (e.g., Zilinskas, et al. (1986), "Phycobilisome structure and function," *Photosynthesis Research,* 10:7–35) and even within rod subelements comprising hexameric double discs (Glazer (1984)). Unlike prior art labels such as fluorescent microspheres and DNA dendrimers, phycobilisomes can therefore perform functions that rely on directional transduction of energy from incident photons to a fluorescent or optoelectronic signal or to a chemical or electrochemical reaction, particularly to perform useful work.

Phycobilisomes of the instant invention can be functionally coupled, preferably by site-directed attachment, to a signal-generating molecule or to a transducer. For example, phycobilisomes can be coupled to a signal-generating molecule such as a second fluorophor (e.g., a donor or acceptor), a light-driven or bioluminescent enzyme (e.g., an ATPase or luciferase) or an artificial reaction center (i.e., a molecule capable of photoinduced charge separation). Alternatively or additionally, they can be attached to an optoelectronic transducer (e.g., photovoltaic cell) so that one region of the phycobilisome (e.g., the terminal acceptor or reaction center) is in direct evanescent or photoelectric communication with the device. The light-harvesting function of phycobilisomes can thus be coupled to an optoelectronic transducer much like a radio antenna is connected to a receiver.

Site-directed attachment of a signal-generating molecule to a particular site on the phycobilisome (e.g., peripheral rod, terminal acceptor, anchor polypeptide, reaction center, or photosystem complex) provides a way to capture. harvested light energy through coupling to other molecular processes (e.g., catalysis, signal transduction, artificial photosynthesis). In other words, molecules or conjugates capable of interacting with particular regions of the phycobilisome (e.g., peripheral rods, core phycobiliproteins, a specific linker or anchor polypeptide or topological site, or a designer group or peptide sequence) can be attached to the desired site in such manner that the resulting phycobilisome conjugate can perform useful functions, particularly functions that depend on the sidedness of the antenna. For example, attachment of a specific recognition site at the terminal acceptor region can provide a target, catalytic site or distinct functional group through which secondary molecules may be attached in a site-specific manner. The antenna function of the phycobilisome can then be modulated or supplemented by the activity of attached molecules, which may be ligands, receptors, signal-generating molecules or simply chemical groups, molecules or complexes foreign to the surface of phycobilisomes as they are found in nature. In addition, the phycobilisome moiety or attached molecules of such conjugates can be used to report interactions (e.g., catalysis, specific binding) between attached molecules and a particular sample or environment.

Immobilization of phycobilisomes to a solid support may be by means of a covalent or non-covalent linkage. Non-covalent methods include, e.g., passive adsorption, affinity-based methods, encapsulation, entrapment and controlled deposition. Immobilization may yield a structurally ordered product. The phycobilisomes may be oriented in a particular manner with respect to the solid support (e.g., "core up" or "core down"). Alternatively the spacing between phycobilisomes on the solid support may be defined or patterned, for example, to form a two-dimensional array or grid.

Methods for physically and chemically patterning surfaces (e.g., by lithography, etching, plasma deposition, plating, bonding and templating techniques) and for preparing biomolecular arrays on surfaces (e.g., by in situ synthesis, robotic dotting and spotting, lithographic methods such as photolithography, piezoelectric and inkjet technologies) are known in the art (e.g., Drmanac, et al. (1989), "Sequencing of megabase plus DNA by hybridization." *Genomics* 4:114–128, Fodor et al. (1991), Pirrung et al. (1994), Crkvenjakov, et al. (1994), "Sequencing by hybridization: Toward large-scale compilation of human cDNA signatures." Human Genome Program, U.S. Department of Energy, Contractor-Grantee Workshop III, Feb. 7–10 (1993), p. 77, Human Genome News (1994), "Workshop on sequencing by hybridization." *Human Genome News* 5(5): 12–13). Arrays, grids or other patterns of a single phycobilisome or conjugate preparation or of multiple different phycobilisome or conjugate preparations can be achieved either by deposition of phycobilisome complexes, phycobilisomes, subassemblies, isolated proteins, peptides, linker polypeptides, anchor polypeptides, ligands or receptors or by in situ synthesis of peptides, polypeptide linkers, nucleic acid molecules or other affinity reagents on solid supports. Attachment surfaces may be modified by any of a wide variety of techniques well-known in the art, such as addition of amino groups by fuming of nitrous acid, bromoacetylation, oxidation by use of plasma, ultraviolet light or an electron beam as energy source in the presence of oxygen and air, chemical grafting, coating with bifunctional reagents (e.g., GA) or polymers (e.g., latex), covalent attachment of linker or spacer molecules, and noncovalent attachment of affinity spacers (e.g., to aromatic groups).

FIG. 1 illustrates a phycobiisome-based biotransducer 100 according to a particularly preferred embodiment of the instant invention. Phycobilisome-based biotransducer 100 comprises a phycobilisome or phycobilisome conjugate 110 functionally coupled to a transducer 120. Typically, the phycobilisome of a phycobilisome-based biotransducer is operatively associated with, attached to, immobilized at, packaged with, or otherwise structurally or functionally inseparable from the transducer. A phycobilisome-based biotransducer can also be a two-component (or multi-component) product or system comprising a transducer component and a disposable, replaceable, reusable or upgradeable phycobilisome-containing cartridge, module, slide, disk, film, layer, fiber, connector, attachment or part that serves as an interface between the phycobilisome and the transducer. In this case, the phycobilisome-containing component is physically separable from the transducer component but must be inserted, attached, rejoined or replaced to form the functionally coupled two-component system capable of performing the intended function. The functionally coupled transducer converts an activity, energy or property of the biological or biomimetic molecule(s) (e.g., the phycobilisome(s) or phycobilisome conjugate(s)) to useful work or information or a detectable signal. Transducers of the instant invention may be electronic, electrical, optical, optoelectronic, electromechanical, electrochemical, photochemical, thermal or acoustical devices and include, without limitation, optical fibers and waveguides, evanescent waveguides, light-addressable potentiometric devices, photovoltaic devices, photoelectric and photochemical and photoelectrochemical cells, conducting and semiconducting substrates, molecular and nanoscale wires, gates and switches, charge-coupled devices, photodiodes, electrical and optoelectronic switches, imaging and storage and photosensitive media (e.g., films, polymers, tapes, slides, crystals and liquid crystals), photorefractive devices, displays, optical disks, digital versatile disks, amperometric and potentiometric electrodes, ion-selective electrodes, field effect transistors, interdigitated electrodes and other capacitance-based devices, piezoelectric and microgravimetric devices, surface acoustic wave and surface plasmon resonance devices, thermistors, and the like. These and other transducers, transduction principles and related devices are known to those of skill in the art (e.g., Taylor, R F (1990) *Biosensors: Technology, Applications, and Markets*, Decision Resources, Inc., Burlington, Mass.), as are techniques for coupling artificial photosynthesis to electrical, electronic and optoelectronic devices (e.g., Gust et al. (1994)). Phycobilisome properties, energies or activities that can be functionally coupled to a transducer include, without limitation, mass, photon absorption or emission, specific binding, catalytic and other signal-generating activities using phycobilisome conjugates, reconstitution and dissociation reactions, and energy transfer to or from molecular species which are functionally coupled to the phycobilisome or phycobilisome complex (e.g., by electronic coupling, preferably by intimate intermolecular proximity and more preferably by covalent attachment, or alternatively by mass or energy transfer accompanying noncovalent interactions such as specific binding).

Transducers of the instant invention typically comprise an organic or inorganic solid support, matrix or surface to which phycobilisomes can be attached either directly or through conductive, reflective, transmissive or passive intermediate(s) (e.g., a wire, lead, fiber, connector, interface, layer, channel or conduit). Transducer surfaces include, without limitation, inorganic substrates such as silicon, silica, silicates, plastics, polymers, graphite and metals used in microfabrication of integrated circuits; glasses, plastics, polymers and quartz as used in optical fibers, planar waveguides and optical disks; thin and thick films and organic and inorganic monolayers, bilayers, multilayer stacks, membranes, polymers and coatings as used in semiconductors, field effect transistors, photoelectric devices and sensors; and microparticles, microvesicles, lipid bilayers, dendrimers, nanostructures, and biocompatible polymers as used in diagnostics, drug delivery and medical devices.

Attachment surfaces may be modified by covalent and noncovalent techniques such as photochemical coupling, plasma treatment, chemical etching, chemical grafting and micromachining processes which are well-known in the art such as lithography, thin film deposition, wet and dry substrate etching, plating, bonding, fusion, templating, injection molding, and the like. Phycobilisomes, phycobilisome complexes and conjugates may be localized at or near a transducer surface by methods including, but not limited to, covalent attachment, hybridization, specific binding, adsorption, encapsulation, controlled deposition, self-assembly or reconstitution of partially dissociated phycobilisomes or isolated constituents in the presence or absence of an immobilized phycobiliprotein linker polypeptide or anchor polypeptide. Alternatively, a phycobilisome constituent (e.g., a linker polypeptide or anchor polypeptide) or a ligand or receptor (e.g., a peptide or nucleic acid) can be synthesized on a surface in situ (e.g., Fodor et al., *Science*, 251:767–772 (1991), Pirrung, et al. (1994), "Preparation of oligonucleotide arrays for hybridization studies," Human Genome Program, U.S. Department of Energy, Contractor-Grantee Workshop III, Feb. 7–10, 1993, p. 173) followed by affinity-based attachment of a phycobilisome. In addition to surface attachment, phycobilisomes may be incorporated or encapsulated within a transducer, e.g., a microvesicle, microparticle, liposome, monolayer, membrane, film, gel or polymer. Phycobilisomes embedded, entrapped or incorporated in this manner can be used to transfer mass, energy, electrons or photons or perform useful work across a membrane or within a segregated phase, environment or vessel. Methods for embedding, entrapping and attaching substances using lipids, micelles, liposomes, membranes and membrane mimetics are well known in the art (U.S. Pat. Nos. 3,966,580 (1976) and 4,490,216 (1984), Betageri et al. (1993), Gregoriadis (1993), Guo et al. (1990), Fendler (1982), Janoffet al. (1988), Machy et al. (1987)).

Functional coupling between a phycobilisome of the invention and a transducer can occur by the transfer of mass, energy, electrons or photons or by coupled chemical or enzymatic reactions that share a common intermediate, mediator or shuttle species. In a preferred mode of operation, a phycobilisome complex or conjugate comprises a photosynthetic reaction center which is functionally coupled to the transducer. A phycobilisome complex comprising a photosynthetic reaction center can be functionally coupled to a transducer by energy transfer and preferably electronic coupling of the charge-separated state of the reaction center. Alternatively, for phycobilisomes lacking a reaction center (e.g., a subassembly or rod), site-specific methods can be used to attach an artificial reaction center (e.g., a signal-generating molecule, complex, or group of molecules, capable of producing a charge-separated state) within energy transferring distance of the phycobilisome terminal acceptor. In this case, the phycobilisome can be functionally coupled to an artificial reaction center which can further be coupled to a transducer by electronic coupling or energy transfer. Functional coupling of phycobilisome complexes and phycobilisomes with artificial reaction centers to transducers can also be achieved or improved using additional coupled signal-generating molecule(s) (e.g., a photosystem, enzyme, cofactor, or molecular mimic). Low molecular weight pigments, donors and acceptors can also be used as mediators or shuttle species to enable or enhance functional coupling to transducers comprising coatings, films, polymers, membranes, monolayers and the like (e.g., Kuhn et al. (1979)).

The invention disclosed herein provides functional coupling of phycobilisomes and phycobilisome complexes to signal-generating molecules and transducers, thereby enabling phycobilisomes and phycobilisome conjugates to serve as optoelectronic components that mimic the light-harvesting efficiency of photosynthetic antenna systems. Since the light harvesting activity of phycobilisomes can be modulated by ambient conditions (e.g., ionic strength, pH, solvents, temperature, moisture, light) and since phycobilisomes can be functionally coupled to signal-generating molecules capable of reporting local events or conditions (e.g., through energy or electron transfer, catalysis or specific binding), phycobilisome-based biotransducers can serve as sensors and actuators responsive to a wide range of conditions, events, ligands, receptors, and signals.

Use of synthetic antenna structures in artificial photosynthesis has been reported (Gust et al. (1993)). Methods have also been described to interface artificial reaction centers with nonbiological structures such as liposomes, micelles, Langmuir-Blodgett films and polymers as well as photoelectric devices such as molecular photodiodes and photoelectrochemical cells (Fujihira M (1991), "Photo-electric conversion with Langmuir-Blodgett films," In: Honda K (Ed.) *Photochemical Processes in Organized Molecular Systems*, Elsevier Science Publishers, Amsterdam, pp. 463–482; Wang, et al. (1992), "Light-induced electron transfer of porphyrin triad for photoelectric conversion," *J. Phys. Chem.*, 96:2886–2891), nanoscale wires (Kittlesen, et al. (1984), "Chemical derivatization of microelectrode arrays by oxidation of pyrrole and N-methylpyrrole: Fabrication of molecule-based electronic devices," *J. Am. Chem. Soc.*, 106:7389–7396), nanofabricated electrodes and conducting substrates (Gust et al. (1994)). This invention provides for the improvement whereby natural photosynthetic structures can be integrated with synthetic devices, i.e., through functional coupling of phycobilisomes to such nonbiological transducers.

Phycobilisome-based assays according to this invention can be detected electrochemically as well as fluorometrically, for example through "phycobilisome electrodes," as alternatives to enzyme electrodes commonly used in amperometric immunosensors. In addition, directional and intimate coupling of phycobilisomes to well-established microelectronic devices (e.g., photodiodes, charge-coupled devices) can provide means for efficient photoelectronic signal transduction on a submicron scale. Within the contemplation of this invention are microminiaturized "biotransducers" such as photoelectric converters, transistors, switches and amplifiers responsive to directional light energy transfer from immobilized, structurally oriented phycobilisomes.

IMMOBILIZATION EXAMPLE 1

Modified Phycobilisomes Immobilized onto Latex Microspheres

FA-treated phycobilisomes and phycobilisome-antibody conjugates ("modified phycobilisomes") quenched with lysine and purified by gel chromatography were immobilized on uniform latex particles either covalently or by passive adsorption. All incubations were performed at room temperature with rotation. Fluorescent and nonfluorescent carboxylate-modified latex microspheres ranging in diameter from 0.03–1 uM were used at final concentrations of 1–10 mg/ml.

Passive adsorption to microspheres was performed for 1–16 hours in 100 mM phosphate (pH 7.2) at immobilization ratios (μg protein/mg particle) ranging from 20–200 μg/mg. Modified phycobilisome-latex suspensions were washed by repeated centrifugation at 8000×g in 100 mM KPi containing 150 mM sodium chloride.

Covalent immobilization was performed at the same protein/particle ratios in a one-step procedure using 1-ethyl-3-(3-dimethylaminopropyl)-carbodiimide (EDAC) in 100 mM MES (pH 6.8). Modified phycobilisomes were rapidly spiked into the particle suspension with mixing, allowed to react for 1–2 hours and washed by centrifugation.

For prolonged storage, immobilized phycobilisomes were post-treated with 1% FA in 100 mM KPi (pH 7.4), quenched with lysine, reduced with sodium cyanoborohydride and washed with 100 mM KPi containing 150 mM sodium chloride and 0.05% sodium azide.

IMMOBILIZATION EXAMPLE 2

Antigens and Antibodies on Paramagnetic Particles

Immobilizations were performed at room temperature according to the following protocol. Amine-modified BIOMAG (Advanced Magnetics) was washed five times with vigorous vortexing and magnetic separation in 10 mM sodium phosphate (NaPi; pH 7.35) at a particle concentration of 5–10 mg/ml. After the final wash, the wet cake was resuspended to 25 mg/ml in 6.25% GA (Sigma) and rotated at room temperature for 3 hours. GA-treated particles were washed six times in NaPi. Washed, GA-activated particles were resuspended with PBS (pH 7.2–7.4) containing the protein to be immobilized at 3–10 mg/ml to yield 100–160 ug protein per mg BIOMAG. BSA was included as a doping agent to adjust the spacing of immunoreactants on BIOMAG particles. An aliquot of the protein solution was retained for determination of immobilization efficiency. The protein-particle slurry was rotated at room temperature for 16–24 hours. Particles were magnetically separated. The supernatant was decanted and retained for estimation of residual protein. Unreacted GA groups were quenched by resuspension of particles to about 10 mg/ml in 1 M glycine (pH 8.0) followed by rotation for one hour. Quenched particles were washed twice in PBS (pH 7.4) and blocked by rotation for two to four hours in PBS containing 2 mg/ml BSA. Blocked particles were washed three times in PBS containing 1 mg/ml BSA, resuspended to a particle concentration of 10 mg/ml and stored at 2–8° C. Working aliquots were washed three times in assay buffer with thorough vortexing at a particle concentration of about 1 mg/ml prior to use to protect against leaching of immobilized reagents with prolonged storage.

IMMOBILIZATION EXAMPLE 3

Antigens and Antibodies Immobilized onto Microtiter Wells

Proteins were passively adsorbed to surface-modified polystyrene microtiter plates by passive adsorption according to the following protocol. Antigens and antibodies were diluted to 2–20 ug/ml in 50 mM carbonate buffer (pH 9.6) or 10 mM sodium phosphate (pH 7.4) in borosilicate glass tubes or 50 ml polypropylene centrifuge tubes immediately before use. Clear polystyrene IMMULON™-4 (Clear polystyrene 96-well microtiter plates) or white MICROLITE™ 2 (opaque white polystyrene 96-well microtiter plates) flat-bottomed microtiter plates (Dynatech) were coated at 100 ul per well for 2 hours at 37° C., 4 hours at room temperature (20–23° C.) or 15–24 hours at 2–8° C. Plates were decanted and washed once by filing wells with wash buffer (PBS (pH 7.4) containing BSA at 1 mg/ml) and decanting. Wells were blocked for 1 hour with 200 μl PBS containing 2 mg/ml BSA and washed five additional times with wash buffer.

ASSAY EXAMPLE 1

Competitive Immunoassay With Photometric Detection

Fifty microliters of sample (assay buffer with or without varying concentrations of mouse immunoglobulin (MIgG)) was added to 12×75 mm glass test tubes arranged in a MAGIC™ (paramagnetic particles) separator unit with a side-pull magnetic base (Corning). One hundred microliters of freshly washed BIOMAG-MIgG was added at particle concentrations ranging from 0.3–10 mg/ml. Tubes were vortexed, and 50 ul phycobilisome-GAM conjugate (molar ratio of 1.5–18 GAM/phycobilisome) was added at phycobilisome concentrations ranging from 1–100 ug/ml (5–500 mAU/ml). The reaction mixture was vortexed and incubated for one hour at room temperature. Particles were separated by placing the Magic™ rack on its magnetic base for five minutes. One hundred sixty microliter aliquots of assay supernatants were transferred to 12×75 mm glass test tubes and subsequently diluted with 100 mM KPi (pH 7.35) to 1 ml for photometric assays or 3 ml for fluorometric assays.

Data presented below represent a checkerboard co-titration of phycobilisome-GAM conjugate and BIOMAG-MIgG, demonstrating that binding is solid phase limited. Percent binding increased dramatically with incremental increases in particle concentration.

| PB-GAM (ug/test) | MIgG ug/test | Supernatant Absorbance (mAU/ml) | | | % binding at [BIOMAG] = | | |
|---|---|---|---|---|---|---|---|
| | | BIOMAG = 30 ug/test | BIOMAG = 100 ug/test | BIOMAG = 300 ug/test | 30 ug/test | 100 ug/test | 300 ug/test |
| 40 | 10 | 210 | 212 | 213 | | | |
| 40 | 0 | 210 | 200 | 173 | 0.0 | 4.7 | 18.8 |
| 12 | 10 | 66 | 68 | 66 | | | |
| 12 | 0 | 63 | 54 | 44 | 4.5 | 20.6 | 33.3 |
| 3 | 10 | 12 | 12 | 12 | | | |
| 3 | 0 | 12 | 10 | 4 | 0.0 | 16.7 | 66.7 |

In separate experiments, conjugate binding was dramatically increased by working at 10-fold higher concentrations of conjugate and solid phase. Assay sensitivity was determined to be below 100 ng/ml MIgG.

ASSAY EXAMPLE 2

Competitive Immunoassay Using Fluorescent Detection

Assays were performed according to the methods of example 6, but reagent concentrations were adapted for fluorescent detection. Data presented below were obtained using 250 ng per test of phycobilisome-GAM conjugate and 250 μg per test of BIOMAG-MIgG. Fluorescence was recorded using 545 nm excitation.

| [MIgG] (ng/test) | $E_{666}$ (cps × $10^{-5}$) | % bound | inhibition (cps × $10^{-5}$) |
|---|---|---|---|
| 0 | 3.74 | 24.3 | — |
| 1 | 4.00 | 19.0 | 0.26 |
| 10 | 4.39 | 11.1 | 0.65 |
| 100 | 4.90 | 0.8 | 1.16 |
| 1,000 | 4.94 | 0.0 | 1.20 |

ASSAY EXAMPLE 3

Displacement Assay Using Phycobilisome Conjugate Prebound to Immobilized Antigen Washed BIOMAG-rabbit IgG (BIOMAG-RIgG) was pretreated with phycobilisome-GAM conjugate (molar ratio of 5/1 GAM/phycobilisome) for two hours at room temperature with mixing. The prebound reagent mixture was washed three times in assay buffer and resuspended to a particle concentration of 400 ug/ml. Five hundred microliter aliquots of prebound reagent were added to 12×75 mm test tubes. The assay was performed by adding 50 ul of sample (buffer with or without MIgG) to the mixture, vortexing, and incubating at room temperature for 60 minutes. After magnetic separation, 500 ul of supernatant was transferred to 2.5 mil 0. I M M for fluorescence measurements.

| [MIgG] (ng/test) | $E^{666}$ | Fluorescence (cps × $10^{-5}$) displacement | % of maximal displacement |
|---|---|---|---|
| 0 | 10.53 | — | |
| 1 | 10.72 | 0.19 | 6.1 |
| 10 | 10.85 | 0.32 | 10.4 |
| 100 | 11.62 | 1.09 | 35.3 |
| 1,000 | 12.46 | 1.93 | 62.5 |
| 10,000 | 13.62 | 3.09 | 100.0 |

A microtiter plate assay in displacement format using the same phycobilisome-GAM conjugate prebound to RIgG-coated wells (20 ug/ml) yielded similar results. The lower displaceable signal is due to the lower solid phase binding capacity of microtiter wells compared to paramagnetic particles.

| [MIgG] (ng/test) | $E^{666}$ | Fluorescence (cps × $10^{-5}$) displacement | % of maximal displacement |
|---|---|---|---|
| 0 | 3.43 | — | |
| 1 | 4.11 | 0.68 | 36.8 |
| 10 | 4.78 | 1.35 | 73.0 |
| 100 | 5.25 | 1.82 | 98.4 |
| 1,000 | 5.28 | 1.85 | 100.0 |

ASSAY EXAMPLE 4

Sandwich (Immunometric) Immunoassay

Reverse sandwich assays were performed by preincubating MIgG with phycobilisome-GAM conjugate followed by capture of phycobilisome-GAM-MIgG complexes with BIOMAG-rabbit anti-mouse antibody (BIOMAG-RAM). This protocol maximizes assay sensitivity by allowing the primary (dynamic) immunoreaction to proceed in solution, improving assay kinetics and minimizing steric constraints. Alternatively, phycobilisome-GAM conjugate was used as a labeled second antibody to detect monoclonal antibody binding to immobilized rabbit IgG (RIgG) as follows.

Fifty microliters of buffer or mouse anti-rabbit antibody (MAR) was preincubated with 50 ul phycobilisome-GAM conjugate (20–80 ug/ml) for 30 minutes. Immune complexes were captured by addition of 100 ul of freshly washed BIOMAG-RIgG at a particle concentration of 10 mg/ml. The reaction was allowed to proceed for 60 minutes prior to magnetic separation. Fluorescence measurements were performed following dilution/transfer of 160 ul assay supernatant to 2.84 ml 0.1 M KPi.

vigorous blotting. One hundred microliters of assay buffer or MIgG (10–1000 ng/well in assay buffer) was added to each well, incubated for one hour at room temperature and

| [MAR] | 1 ug/test PBsome-GAM | | 2 ug/test PBsome-GAM | | 4 ug/test PBsome-GAM | |
|---|---|---|---|---|---|---|
| (ng/test) | $E_{666} \times 10^{-6}$ | % bound | $E_{666} \times 10^{-6}$ | % bound | $E_{666} \times 10^{-6}$ | % bound |
| 0 | 1.483 | 0 | 2.400 | 0 | 4.147 | 0 |
| 0.1 | 1.392 | 6.1 | 2.322 | 3.3 | 4.196 | 0 |
| 1.0 | 1.142 | 23.0 | 1.786 | 25.6 | 3.430 | 17.3 |
| 10 | 0.823 | 44.5 | 1.289 | 46.3 | 2.107 | 49.2 |
| 100 | 0.697 | 53.0 | 0.992 | 58.7 | 1.709 | 58.8 |
| 1000 | 0.615 | 58.5 | 0.967 | 59.7 | 1.511 | 63.6 |

ASSAY EXAMPLE 5

Microtiter-Based Immunoassay With Visual Detection

Competitive Assays: White polystyrene MICROLITE™ 2 microtiter plates (Dynatech) were coated by passive adsorption for 15 hours at 2–80 C with 2–20 ug/ml MIgG in 10 mM sodium phosphate (pH 7.35). Supernatants were aspirated. Wells were incubated for 60 minutes at room temperature with 200 ul blocking buffer (10 mM phosphate-buffered isotonic saline (PBS, pH 7.4) containing 100 mM potassium phosphate (pH 7.35), 2 mM sodium azide and 2 mg/mil BSA) and washed six times with 250 ul wash buffer (PBS containing 1 mg/ml BSA). After the final wash, plates were inverted on paper towels and drained by blotting vigorously. Fifty microliters of assay buffer (PBS containing 100 mM potassium phosphate (pH 7.35), 2 mM sodium azide and 1 mg/ml BSA) or MIgG (10–1000 ng/well in assay buffer) was added to each well followed by 50 ul of phycobilisome-GAM at 0.5–10 ug/well. Plates were incubated for one hour with shaking at room temperature, decanted, and inspected before and after washing three times with assay buffer. Phycobilisome-GAM binding to immobilized MIgG could be visually discriminated (both before and after plates were washed) as a purplish-pink coating on the bottom and lower insides of wells under the following conditions:
  1. MIgG coating concentration>0.5 ug/well; and
  2. phycobilisome-GAM conjugate>1 ug/well; and
  3. competing [soluble MIgG]<10 ng/well.

Significant nonspecific binding (bound color at 1 ug/well soluble MIgG) was not visibly apparent in washed plates even at the highest concentrations of phycobilisome-GAM. Visually detectable specific binding (color difference ±1 g/well MIgG) was most dramatically apparent in wells treated with the highest coating and conjugate concentrations (10–20 ug/ml coating×5–10 ug/well phycobilisome-GAM). Under these conditions, the visual detection limit for MIgG was 10–100 ng/test, corresponding to $10^{-12}$–$10^{-13}$ moles/test (about $10^{-9}$ M MIgG).

Sandwich Assays: White polystyrene MICROLITE™ 2 microtiter plates (Dynatech) were coated for 15 hours at 2–8° C. with 2–20 ug/ml affinity-purified RAM (H+L) antibody in 10 mM sodium phosphate (pH 7.35). Supernatants were aspirated and wells were incubated with 200 ul blocking buffer (as per competition assays) for one hour at room temperature followed by six washes with 250 ul wash buffer (PBS containing 1 mg/ml BSA). After the last wash, plates were inverted and drained on paper towels with vigorous blotting. One hundred microliters of assay buffer or MIgG (10–1000 ng/well in assay buffer) was added to each well, incubated for one hour at room temperature and aspirated. Wells were washed three times with 250 ul wash buffer. Phycobilisome-GAM conjugate was added at 0.5–10 ug/well in 100 ul assay buffer, incubated for two hours at room temperature with shaking, decanted, and inspected before and after three was with assay buffer. With and without washing, bound phycobilisome-GAM could be visually discerned in wells exposed to MIgG under the following conditions:
  1. RAM coating at >0.2 µg/well; and
  2. [MIgG]>10 ng/well; and
  3. [phycobilisome-GAM] at 1.5–10 µg/well, depending on RAM and MIgG concentrations.

Prior to washing, visual discrimination of wells exposed to 10 ng/ml MIgG compared to assay buffer was marginal. Washing provided only a minor improvement in resolution. No effort was made to optimize the visual detection limit of immunometric microtiter assays by increasing solid phase binding capacity or conjugate concentration, selecting a higher affinity tracer antibody, modifying the assay protocol or buffer composition, or determining preferred conditions for inspection of the bound phase under UV illumination.

ASSAY EXAMPLE 6

Immunochromatographic Dipstick With Visual Detection

Competitive Assay Configuration: MIgG was covalently immobilized to localized zones on aldehyde-treated modified polysulfone membranes as follows. ULTRABIND™ (modified polyethersulfone affinity membrane) US800 unsupported membrane with an effective pore size of 0.8 uM (Gelman Sciences) was cut into 20 cm×6 cm sections. MIgG (2–10 mg/ml in 10 mM phosphate-buffered isotonic saline (PBS), pH 7.2, containing 0.1% sodium azide) was manually spotted by graduated capillary pipet (Drummond Scientific) at 4 ul per linear centimeter along a longitudinal line pencilled midway across each section (3 cm from either edge). After air drying for 30 minutes, membranes were incubated with gentle shaking for one hour at room temperature in 50 ml blocking buffer consisting of 1% BSA in 10 mM PBS (pH 7.4), rinsed twice in 100 ml PBS (pH 7.2) containing 0.1% BSA and air dried for 3 hours. Rinsed, dried membranes were then washed for one hour with shaking in PBS (pH 7.2) containing 0.2% Tween 20 and allowed to dry overnight at room temperature.

Phycobilisome-GAM conjugate was applied to MIgG-modified membranes as follows. Dry, washed membrane sections were cut width-wise into 1×6 cm strips. Ten microliters of phycobilisome-GAM conjugate (2.5 $AU_{545}$/ml)

comprising approximately 0.5 mg/ml stabilized *P. cruentum* phycobilisomes and 10 ug/ml immunologically active GAM in 0.5 M KPi (pH 7.35) containing 0.1 M sucrose was applied over about 1 square centimeter of each 1×6 cm strip midway between one end and the central transverse line of immobilized MIgG. Conjugate-treated strips were air-dried for 30 minutes before use.

Immunochromatographic MIgG dipsticks were evaluated by contacting the conjugate-treated ends of dried strips to buffer (PBS (pH 7.4) containing 1 mg/ml BSA) or MIgG (1 ug/ml in buffer) and allowing samples to wick up strips by capillary action. When the fluid front had migrated 3.5 cm up the buffer-treated strip (about 10 minutes), a purple-pink band appeared at the immobilized MIgG line (3 cm) and grew progressively more intense as the strip became entirely saturated with buffer (about 20 minutes). No band was apparent in strips exposed to MIgG-containing buffer, indicating that binding of phycobilisome-GAM to immobilized MIgG was substantially inhibited by soluble MIgG.

Inspection of strips in a darkroom under long-wavelength (365 nm) ultraviolet illumination failed to reveal localized phycobilisome-GAM fluorescence in MIgG-treated dipsticks. In buffer-treated dipsticks, phycobilisome-GAM bound to immobilized MIgG was apparent as an intense, fluorescent-red band against a dark blue background. This fluorescent band disappeared after strips were air-dried. When water was applied to the visible band on dry, buffer-treated strips, intense localized red (phycobilisomes) and mobile orange (B-PE) fluorescent phases were observed, suggesting partial dissociation of GA-treated phycobilisomes with drying and re-wetting. Similar results were obtained by fluorometric evaluation of phycobilisome-GAM conjugates before and after freeze-drying. The ratio of 666/573 nm emission with 545 nm excitation decreased markedly with drying and reconstitution, suggesting significant uncoupling of fluorescence energy transfer, unless conjugates were pretreated with sucrose or other protectants. Since isolated B-PE is a more intense fluorophore than APC (the terminal acceptor of *P. cruentum* phycobilisomes), dissociation of phycobilisomes between conjugate binding and detection steps provides a means to amplify the fluorescent signal and increase assay sensitivity.

Sandwich Assay Configuration: Immunometric MIgG dipsticks were prepared by methods substantially equivalent to those for competitive dipsticks, except affinity-purified RAM antibody ((H+L chain)-specific; OEM Concepts) was immobilized to ULTRABIND™ US800 membranes in place of MIgG. Ten microliters of RAM (2 mg/ml) per linear centimeter was spotted width-wise across 10×6 cm membrane sections, which were then blocked, rinsed, washed and cut into 1×6 cm strips as per MIgG-immobilized membranes. Ten microliters of phycobilisome-GAM conjugate (5.1 $AU_{545}$/ml) comprising approximately 1 mg/ml stabilized *P. cruentum* phycobilisomes and 20 ug/ml immunologically active GAM in 0.5 M KPi (pH 7.35) containing 0.2 M sucrose was applied midway between one end and the immobilized RAM line as per competitive dipsticks, and strips were air-dried before use.

Sandwich MIgG dipsticks were evaluated by contacting the conjugate-treated end to PBS-BSA buffer with or without MIgG (1 ug/ml) and allowing the sample to saturate strips by capillary action (about 20 minutes). A distinct purple-pink band formed at the immobilized RAM line in MIgG-treated dipsticks, but not in buffer-treated controls. These results demonstrate specific binding of a soluble phycobilisome conjugate in an immunometric assay with a visual detection limit below $6 \times 10^{-9}$ M.

ASSAY EXAMPLE 7

Direct Quantification of Bound Oligonucleotide

A synthetic oligonucleotide is produced by either PCR or use of a nucleic acid synthesizer. An amine group is introduced on the end of this by a standard method. This amine is then biotinylated using NHS ester linked biotin reagents (e.g., Pierce Chemical's sulfo-NHS-biotin). The biotinylated oligonucleotide is diluted in buffer in a serial manner and then placed on nitrocellulose or other solid media commonly used for nucleic acid transfer (e.g., nylon or supported nitrocellulose). This is done either by dotting on a known amount of material or using an apparatus made for quantitative transfer of nucleic acid such as a dot or slot blotter. The material is then covalently linked to the solid phase using either UV crosslinking or drying in a vacuum oven at 85° C. This is then blocked with materials to prevent nonspecific binding of the labeled binding reagents. Phycobilisomes conjugated directly to streptavidin or avidin as described above are then added to a buffer and provided to a blot containing the immobilized, biotinylated nucleic acid. These are allowed to react with gentle shaking to allow interaction of biotin and streptavidin. Blots are then washed extensively in buffers with or without the addition of materials to facilitate release of nonspecifically bound materials. The bound material is then visualized either directly or with an instrument to facilitate photometric or fluorometric detection.

ASSAY EXAMPLE 8

Indirect Quantification of Bound Oligonucleotide via Hybridization

A synthetic oligonucleotide (A) and its complementary strand (A') are produced by either PCR or use of a nucleic acid synthesizer. The test oligonucleotide (A) is diluted in buffer in a serial manner and then placed on nitrocellulose or other solid media commonly used for nucleic acid transfer (e.g., nylon and supported nitrocellulose). This is done either by dotting on a known amount of material or using an apparatus made for quantitative transfer of nucleic acids such as a dot or slot blotter. The material is then covalently linked to the solid phase using either UV crosslinking or drying in a vacuum oven at 85° C. This is then blocked with materials to prevent nonspecific binding of the labeled binding reagent. An amine group is introduced on the end of the complementary strand (A') by a standard method. This amine is then biotinylated using NHS ester linked biotin reagents (e.g., Pierce Chemical's sulfo-NHS-biotin). The biotinylated complementary strand is then hybridized with the immobilized test strand using any of the standard hybridization techniques. The blot is washed well to remove the free biotinylated probe and then reacted with a secondary labeling system using phycobilisomes labeled with streptavidin or avidin. Phycobilisomes conjugated directly to streptavidin or avidin as described above are then added to a buffer and provided to a blot containing the specifically bound, biotinylated complementary oligonucleotide. These are allowed to react with gentle shaking to allow interaction of biotin and streptavidin. Blots are then washed extensively in buffers with or without the addition of materials to facilitate release of nonspecifically bound materials. The bound material is then visualized either directly or with an instrument to facilitate photometric or fluorometric detection.

ASSAY EXAMPLE 9

Use in DNA Blotting (Southern) Hybridization

Large molecular weight DNA is transferred to nitrocellulose or other similar solid phase material commonly used for DNA transfer. This is done using either capillary, electrophoretic or vacuum methods of transfer. The DNA is fixed using UV or heat as normally done. This is then hybridized with a biotinylated probe to a specific DNA sequence at 65° C. to allow the complementary probe to bind to the target sequence. This is washed to remove nonspecifically bound DNA, and the blot is reacted with avidin- or streptavidin-labeled phycobilisomes to specifically label hybridized biotinylated probes. This is washed to remove nonspecifically bound material and visualized by eye or by photometric or flurometric instrumentation. This type of assay can also be done using protein/antibody or receptor/ligand links in place of the avidin/biotin links.

ASSAY EXAMPLE 10

Use in RNA Blotting (Northern) Hybridization

RNA blots are probed in a manner analogous to that described for DNA. In this case either a synthetic DNA or RNA oligonucleotide is used as the probe and is labeled either directly or indirectly with phycobilisomes.

ASSAY EXAMPLE 11

Use in Protein Detection (Western Blotting)

After protein electrophoresis, the protein is transferred to nitrocellulose or other solid matrices using electric current for transfer. The protein is then detected either directly using a phycobilisome conjugated to an antibody against the target protein or indirectly using a phycobilisome attached to biotin or anti-antibody as a secondary label.

ASSAY EXAMPLE 12

Enhancement of Signal Using Deterioration (Dissociation) of the Phycobilisome When not concerned with Stokes shift, signal enhancement may be obtained by proceeding with the binding and removal of nonspecific binding as in Assay Example 11. Then the sample is exposed to distilled water to break down the phycobilisome into constituent phycobiliproteins. Freed phycobiliproteins then are free to flourescently emit light at their own emission maximum versus being funneled through a terminal emitter such as allophycocyanin.

Phycobilisomes isolated from *Porphyridium cruentum*, which are composed mostly of phycoerythrin, were conjugated to goat anti-mouse antibody (GAM). Mouse IgG was immobilized in a strip on a small piece of ULTRABIND 800™ (Gelman) using the activated groups on the membrane for covalent attachment of the mouse IgG. This was dried, blocked with BSA, dried again, then used in a dipstick format in the test system containing the phycobilisome-GAM. A line of conjugate was placed near the bottom of the paper after protein blocking was done and allowed to dry. The paper was dipped in a buffer (containing phosphate, salt and a small amount of BSA) and as the buffer passed the dried-on conjugate, the conjugate was completely solubilized and moved cleanly over the covalently bound mouse IgG. The conjugates bound to the mouse IgG, and what was not bound was removed by a wash in the loading buffer. This was visualized using a ultraviolet lamp and very nice red color was observed on the band where the mouse IgG had been immobilized. If the paper was allowed to dry and then distilled water was placed on the paper, a rapid change in fluorescent emission was seen as the phycobilisome broke down and B-PE emission became dominant. This was a much more intense color than that seen using the intact phycobilisome. The exact amount of amplification was not determined.

ENERGY TRANSDUCTION EXAMPLE 1

Biotransducer Comprising a Phycobilisome Functionally Coupled to an Optical Fiber Phycobilisomes isolated from *P. cruentum* and stabilized with FA are site-specifically labeled near the terminal acceptor of the core complex using affinity purified rabbit anti-APC antibody (RAAPC; Accurate Chemical & Scientific Corporation, Westbury N.Y.). Affinity purified goat anti-rabbit IgG (GAR; OEM Concepts, Toms River, N.J.) is immobilized on 1×60 mm cylindrical quartz fibers with polished ends by passive adorption in a PBS buffer for at least two hours at room temperature. (In an alternative mode of operation, GAR is covalently attached through carbohydrate groups in the Fc region to hydrazide-modified fibers, thereby maximizing the immunologic availability of antigen-combining sites.) Coated fibers are washed thoroughly in PBS-BSA and air-dried prior to use in binding assays. Specific binding of the RAAPC-phycobilisome conjugate to GAR-coated fibers is detected through evanescent excitation of bound phycobilisomes and evanescent capture of emitted energy using a portable fluorometer (ORD Inc., North Salem, N.H.) equipped with 550 nm excitation and 660 nm emission band-pass filters. Fibers are mounted vertically in a flow cell having a capacity of 46 ul and perfused with PBS-BSA at a rate of 184 ul/minute. Fluorescent light is collected and guided by the fiber and detected by photodiodes arranged so as to distinguish between surface-bound fluorescence (from smaller angles) and background light (from larger angles). Evanescent detection principles for both planar waveguides (e.g., Badley, et al. (1987), "Optical biosensors for immunoassays: the fluorescence capillary-fill device," *Phil. Trans. R. Soc. Lond.*, B316:143–160) and optical fibers (e.g., Rogers, et al. (1992), "Fiber-Optic biosensors based on total internal-reflection fluorescence," In: *Biosensor Design and Application*, (Eds. P. R. Mathewson and J. W. Finley), *Am. Chem. Soc. Symp. Ser.*, 511, Chapter 13, pp. 165–172) are well-known in the art. The transducer in this example is the optical fiber operatively coupled through its evanescent field to photodiode(s) capable of generating an electronic signal (voltage). RAAPC-phycobilisome binding to the GAR-coated fiber is dose-dependent and competitively inhibited by either unlabeled GAR or RAAPC antibodies. This example therefore illustrates a fiberoptic sensor that relies on functional coupling of a phycobilisome to a transducer for detection of an antibody.

A phycobilisome-based biotransducer relying on regio-specific attachment and functional coupling of phycobilisomes to an optical fiber is prepared and used as follows. Anchor polypeptide is isolated by complete dissociation and column chromatography from *P. cruentum* phycobilisomes and passively adsorbed to quartz fibers. The rod-core linker polypeptide is also isolated from *P. cruentum* phycobilisomes by dissociation and chromatography and is biotinylated by established methods using a long-chain N-hydroxysuccinimide ester of biotin (Pierce Chemical Company, Rockford, Ill.). APC-containing core complexes are then reconstituted on anchor protein-coated quartz fibers from isolated phycobiliproteins and linker polypeptides. The reconstituted, immobilized core complexes are then crosslinked in place using GA (0.05–0.50%). Excess GA is removed by repeated washes with PBS. Streptavidin (2–50 ug/ml in PBS) is then conjugated to reactive aldehyde groups on the immobilized core complexes. Fibers are then quenched with lysine, blocked with PBS-BSA, washed extensively and air-dried. Modified P. cruentum phycobilisomes comprising a single rod are reconstituted from isolated phycobiliproteins, intra-rod linker polypeptides and biotinylated rod-core linker polypetides. These reconstituted rods, having a biotinylated rod-core linker polypeptide near the terminal acceptor, are then stabilized, quenched and reduced using FA, lysine and sodium cyanoborohydride (cf. "Detailed Description of Preferred Embodiments" supra). Specific binding of stabilized, biotinylated phycobilisome rods to streptavidin-modified immobilized core complexes is measured by evanescent excitation and detection using 550 nm and 660 nm band-pass filters as described above. In the absence of unlabeled biotin, specific binding of biotinylated rods to streptavidin-modified immobilized core complexes results in efficient evanescent excitation at 550 nm and collection of emitted fluorescence at 660 nm. Unlabeled biotin added to the flow cell competitively inhibits binding of the biotinylated rods, interrupting evanescent excitation. Unlabeled avidin or streptavidin also competitively inhibits specific binding and evanescent excitation. This phycobilisome-based biotransducer therefore serves as a prototypical example of an optoelectronic sensor capable of detecting either ligands (i.e., biotin and derivatives) or receptors (i.e., streptavidin, avidin and derivatives). Optimal performance of this phycobilisome-based fiberoptic sensor requires regio-specific conjugation to phycobilisomes (i.e., biotinylation of rods) and/or regio-specific attachment of phycobilisomes to transducers (i.e., immobilization of core complexes). Site-specific attachment enables directional energy transfer and functional coupling to the transducer. Similar "reconstitution-based" sensing principles can be developed using either algal or cyanobacterial phycobilisome subassemblies prepared, e.g., by partial dissociation using methods adapted from Rigbi et al. (1980), Gantt et al. (1979) and Nies et al. (1981) with or without covalent stabilization.

ENERGY TRANSDUCTION EXAMPLE 2

Biotransducer Comprising a Phycobilisome Functionally Coupled to a Photodiode

Anchor polypeptide is purified from P. cruentum phycobilisomes as described in Energy Transduction Example 1 and passively adsorbed to the hydrophobic surface (approximately 4 mm$^2$) of polymer coated indium phosphide photodiodes selected for maximal responsiveness (signal-to-noise ratio) at 600–700 nm. P. cruentum core complexes are then reconstituted on anchor protein-coated photodiodes by exposing the surface to a mixture of isolated phycobiliproteins and linker polypeptides. The reconstituted, immobilized core complexes are then crosslinked in place with GA, excess GA is removed by rinsing, and streptavidin is conjugated to unreacted aldehyde groups on the immobilized core complexes. Photodiodes are then quenched with lysine, blocked with PBS-BSA, rinsed extensively and air-dried. Biotinylated rod-core linker polypeptide is prepared by methods described in Energy Transduction Example 1. Specific binding of biotinylated phycobilisome rods to streptavidin-modified immobilized core complexes is detected as electrical current following photodiode excitation through a 550/30 nm band pass filter. In the absence of unlabeled biotin, specific binding of biotinylated rods to streptavidin-modified immobilized core complexes results in efficient energy transfer from rods to core complexes to the photodiode, as evidenced by a voltage-dependent current response of the diode. Immobilized core complexes sensitized by specifically bound rods are functionally coupled to the photodiode, as demonstrated by the dose-dependent increase in current generated by the photodiode when increasing concentrations of biotinylated rods are added. Addition of unlabeled biotin to biotinylated rod samples results in dose-dependent attenuation of photodiode current due to competitive inhibition of biotinylated rod binding. Unlabeled avidin and streptavidin also competitively inhibit photodiode output.

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, immunology, semiconductors, fluorescence, instrumentation, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention claimed is:

1. A system for processing a light signal comprising:
   conversion means for receiving ultraviolet or visible light and directionally transferring light energy of said light and
   processing means for receiving and processing said directionally transferred light energy.

2. The system of claim 1, wherein said processing means comprises an optical fiber operative to transmit said light signal energy.

3. The system of claim 1, wherein said processing means comprises a photosensor.

4. The system of claim 1, wherein said conversion means comprises a photon conversion means comprising a supramolecular light-absorbing structure.

5. The system of claim 1, wherein said processing means comprises a waveguide.

6. The system of claim 1, wherein said processing means comprises an optoelectronic device.

7. The system of claim 1, wherein the processing means comprises a photovoltaic cell.

8. The system of claim 1, wherein the conversion means comprises phycobiliproteins specifically connected by linker polypeptides.

9. A system for processing electromagnetic radiation comprising:
   conversion means for receiving electromagnetic radiation and converting said electromagnetic radiation into light energy having a desired property; and
   processing means for receiving and processing said light energy.

10. The system of claim 9, wherein said processing means comprises a phycobilisome.

11. The system of claim 9, wherein said processing means comprises an optical fiber.

12. The system of claim 9, wherein said processing means comprises a waveguide.

13. The system of claim 9, wherein said processing means comprises an optoelectronic device.

14. The system of claim 9, wherein said processing means comprises a photosensor.

15. The system of claim 9, wherein said electromagnetic radiation comprises ultraviolet or visible light.

16. The system of claim 15, wherein said light energy is red-shifted relative to the received electromagnetic radiation.

17. The system of claim 9, further comprising a transducer.

18. The system of claim 9, wherein the conversion means includes a structure comprising a phycobilisome, the phycobilisome comprising two or more phycobiliproteins.

19. The system of claim 18, wherein the two or more phycobiliproteins are coupled by one or more linker polypeptides.

20. The system of claim 19, wherein the two or more phycobiliproteins are in a particular orientation based on the one or more linker polypeptides.

21. The system of claim 19, wherein the particular orientation facilitates energy transfer between at least two of the two or more phycobiliproteins.

22. The system of claim 1 for processing a light signal comprising:
   at least one phycobilisome for receiving ultraviolet or visible light and directionally transferring light energy of said light, wherein the at least one phycobilisome comprises at least one of: an isolated, soluble, stabilized phycobilisome;
   a phycobilisome conjugated to a molecular species selected from the group consisting of ligands, receptors, and signal-generating molecules; and
   a phycobilisome immobilized on a manufactured solid support; and
   processing means for receiving and processing said directionally transferred light energy.

23. The system of claim 22, wherein the processing means comprises an electronic transducer.

24. The system of claim 23, wherein the electronic transducer comprises an optoelectronic transducer.

25. The system of claim 22, wherein the at least one phycobilisome comprises at least one isolated, soluble, stabilized phycobilisome.

26. The system of claim 22, wherein the at least one phycobilisome comprises at least one phycobilisome conjugated to a molecular species selected from the group consisting of ligands, receptors, and signal-generating molecules.

27. The system of claim 22, wherein the at least one phycobilisome comprises at least one phycobilisome immobilized on a manufactured solid support.

* * * * *